US008029778B2

(12) United States Patent
Seya et al.

(10) Patent No.: US 8,029,778 B2
(45) Date of Patent: Oct. 4, 2011

(54) METHODS OF USING TICAM-1, AN ADAPTER PROTEIN THAT BINDS TOLL-LIKE RECEPTOR 3

(75) Inventors: Tsukasa Seya, Sapporo (JP); Misako Matsumoto, Sapporo (JP); Hiroyuki Oshiumi, Osaka (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 12/385,127

(22) Filed: Mar. 31, 2009

(65) Prior Publication Data

US 2010/0087510 A1   Apr. 8, 2010

Related U.S. Application Data

(62) Division of application No. 10/536,802, filed as application No. PCT/JP03/14854 on Nov. 20, 2003, now Pat. No. 7,582,437.

(30) Foreign Application Priority Data

Nov. 29, 2002 (JP) .................................. 2002-349015

(51) Int. Cl.
*A61K 48/00* (2006.01)
*C12P 21/04* (2006.01)
*C12N 5/02* (2006.01)
*G01N 33/567* (2006.01)

(52) U.S. Cl. ...................... 424/93.2; 435/70.1; 435/70.3; 435/455; 435/69.1; 435/7.21; 530/351; 536/23.5

(58) Field of Classification Search .......................... None
See application file for complete search history.

(56) References Cited

U.S. PATENT DOCUMENTS

| 7,227,007 B2 | 6/2007 | Matsuda et al. |
| 2003/0143540 A1 | 7/2003 | Matsuda et al. |
| 2003/0170719 A1 | 9/2003 | Matsuda et al. |
| 2007/0105198 A1 | 5/2007 | Matsuda et al. |

FOREIGN PATENT DOCUMENTS

| EP | 1354950 | 10/2003 |
| WO | 00/78954 | 12/2000 |
| WO | 02/053737 | 7/2002 |
| WO | 2004/044201 | 5/2004 |

OTHER PUBLICATIONS

Rubanyi, biol. Aspects Med. 2001, vol. 22, pp. 113-142.*
Juengst, British Medical Journal, 2003, vol. 326, pp. 1410-1411.*
Matsumoto. Biochemical and Biophysical Research Communication, 2002, vol. 293, pp. 1364-1369.*
Akazawa et al, Cancer Research, 2004, vol. 64, pp. 757-764.*
Jablonska et al, The Journal of Clinical Investigation, 2010, vol. 120, No. 4, pp. 1151-1163.*
Dunn et al, Nature Reviews, 2006, vol. 6, pp. 836-848.*
Anderson "Human gene therapy" Nature 392:25-30 (1998).
Crystal "Transfer of genes to humans: Early lessons and obstacles to success" Science 270:404-410 (1995).
Kaufman et al. "Transgenic analysis of a 100-kb human β-globin cluster-containing DNA fragment propagated as a bacterial artificial chromosome" Blood 94:3178-3184 (1999).
Wang et al. "Rapid analysis of gene expression (RAGE) facilitates universal expression profiling" Nucl. Acid Res. 27:4609-4618 (1999).
Office Action in related U.S. Appl. No. 12/385,128, mailed Jan. 12, 2010.
Akira et al. "Murine TIR domain-containing adaptor inducing interferon-beta protein" GENESEQ Accession No. AD033467 from WO 2004/044201 (Aug. 2004).
Alexopoulou et al. "Recognition of double-stranded RNA and activation of NF-κB by Toll-like receptor 3" Nature 413:732-738 (2001).
Fitzgerald et al. "Mal (MyD88-adapter-like) is required for Toll-like receptor-4 signal transduction" Nature 413:78-83 (2001).
Horng et al. "TIRAP: An adapter molecule in the Toll signaling pathway" Nature Immunol. 2:835-841 (2001).
Imler et al. "Toll signaling: The TIReless quest for specificity" Nature Immunol. 4:105-106 (Feb. 2003).
Kawai et al. "Lipopolysaccharide stimulates the MyD88-independent pathway and results in activation of IFN-regulatory factor 3 and the expression of a subset of lipopolysaccharide-inducible genes" J. Immunol. 167:5887-5894 (2001).
Lal et al. "TICAM1 protein (fragment)" UNIPROT Accession No. Q8JZVO from WO 00/78954 (Oct. 2002).
Lazar et al. "Transforming growth factor α: Mutation of aspartic acid 47 and leucine 48 results in different biological activities" Mol. Cell. Biol. 8:1247-1252 (1988).
Matsuda et al. "Human NF-κB activating protein" GENESEQ Accession No. ABP61500 from WO 02/053737 (Sep. 2002).
Matsumoto et al. "Establishment of a monoclonal antibody against human Toll-like receptor 3 that blocks double-stranded RNA-mediated signaling" Biochem. Biophys. Res. Comm. 293:364-1369 (May 2002).
Oshiumi et al. "TICAM-1, an adaptor molecule that participates in Toll-like receptor 3-mediated interferon-beta induction" Nature Immunol. 4:161-167 (Feb. 2003).

(Continued)

*Primary Examiner* — Bridget E Bunner
*Assistant Examiner* — Fozia Hamud
(74) *Attorney, Agent, or Firm* — Nixon & Vanderhye P.C.

(57) ABSTRACT

A novel adaptor protein and its gene are provided. The novel adaptor protein has a property of binding to mammalian Toll-like receptor 3, which controls type I interferon production that is effective for prevention/treatment of viral infectious disease such as hepatitis B, hepatitis C, and the like, treatment of tumors, and the other purposes. Novel adaptor protein TICAM-1, which has an amino acid sequence set forth in SEQ ID NO: 2 or 4, specifically binds to the mammalian Toll-like receptor 3 and induces production of type I interferon. A mutant of the adaptor protein TICAM-1 has similar properties, provided that it has TIR domain (an amino acid sequence ranging from 394-position to 532-position in the amino acid sequence set forth in SEQ ID NO: 2 or an amino acid sequence ranging 396-position to 534-position in the amino acid sequence set forth in SEQ ID NO: 4). The gene is a gene encoding the adaptor protein TICAM-1.

7 Claims, 16 Drawing Sheets

OTHER PUBLICATIONS

Oshiumi et al. "TICAM-1" UNIPROT Accession No. Q80UF7 from the above document (Jun. 2003).

Wells "Additivity of mutational effects in proteins" Biochemistry 29:8509-8517 (1990).

Yamamoto et al. "Cutting edge: A novel Toll/IL receptor domain-containing adapter that preferentially activates the IFN-β promoter in the Toll-like receptor signaling" J. Immunol. 169:6668-6672 (Dec. 2002).

Yamamoto et al. "TIR domain containing adaptor inducing interferon-beta (TICAM-1) putative NFκB activating protein" UNIPROT Accession No. Q8IUC6 from the above document (Mar. 2003).

International Search Report for PCT/JP2003/014854, one page, dated Jan. 13, 2004.

Int'l Preliminary Report on Patentability for PCT/JP2003/014854, five pages, dated Jul. 7, 2004.

Supplementary search report for EP 03774108, six pages, dated Apr. 28, 2006.

Su et al. "A gene atlas of the mouse and human protein-encoding transcriptomes" Proc. Natl. Acad. Sci. USA nol. 101, No. 16, pp. 6062-6067 (Apr. 2004).

Office Action in related Canadian Appln. No. 2,507,716, three pages, mailed Apr. 30, 2009.

* cited by examiner

NF−κB

Interferon β

SD-Trp-Leu-His-Ade plate pGBKT7-TLR3
pGADT7 pGBKT7-TLR3
pGADT7-TICAM-1 pGBKT7-TLR4
pGADT7-TICAM-1 pGBKT7
pGADT7-TICAM-1

FIG. 5

```
TICAM-1.hu    MACTGPSLPSAFDILGAAGQDKLLYLKHKLKTPRPGCQGQDLLHAMVLLKLGQETEARIS
TICAM-1.mu    MDNPGPSLRGAFGILGALERDRLTHLKHKLGSLCSGSQESKLLHAMVLLALGQDTEARVS
              * .****.**.****  :*:* :***** :  .*.* ..******** ***.****:*

TICAM-1.hu    LEALKADAVARLVARQWAGVDSTEDPEEPPDVSWAVARLYHLLAEEKLCPASLRDVAYQE
TICAM-1.mu    LESLKMNTVAQLVAHQWADMETTEGPEEPPDLSWTVARLYHLLAEENLCPASTRDMAYQV
              **:** ::**:***:***.::**.*******:**:**********:***** **:***

TICAM-1.hu    AVRTLSSRDDHRLGELQDEARNRCGWDIAGDPGSIRTLQSNLGCLPPSSALPSGTRSLPR
TICAM-1.mu    ALRDFASQGDHQLGQLQNEAWDRCSSDIKGDPSGFQPLHSHQGSLQPPSASPAVTRSQPR
              *:* ::*:.**:**:**:** **  **. ** ***..::.*:*: *.* *.** *:  *** **

TICAM-1.hu    PIDGVSDWSQGCSLRSTGSPASLASNLEISQSPTMPFLSLHRSPHGPSKLCDDPQASLVP
TICAM-1.mu    PID-TPDWSWGHTLHSTNSTASLASHLEISQSPTLAFLSSHHGTHGPSKLCNTPLDTQEP
              *** ..*** * :*:**.*.*****:********:.**.**:::*.:.*****: *  : *

TICAM-1.hu    EPVPGGCQEPEEMSWPPSGEIASPPELPSSPPPPGLPEVAPDATSTGLPDTPAAPETSTNY
TICAM-1.mu    QLVPEGCQEPEEISWPPSVETSVSLGLP--HEISVPEVSPEEASPILPDALAAPDTSVHC
              : ** *******:***** *  : .**  .:.***:*:*.*  ***: ***:**.

TICAM-1.hu    PVECTEGSAGPQSLPLPILEPVKNPCSVKDQTPLQLSVEDTTSPNTKPCPPTPTTPETSP
TICAM-1.mu    PIECTELSTNSRSPLTSTTESVGKQWPITSQRSPQVPVGDDSLQNTTSSSPPAQPPSLQA
              *:**** *:...:*  . *.*   :. *.*:**: *: **....*...*.  ..

TICAM-1.hu    PPPPPPP----SSTPCSAHLTPSSLFPSSLESSS-EQKFYNFVILHARADEHIALRVREK
TICAM-1.mu    SPKLPPSPLSSASSPSSYPAPPTSTSPVLDHSETSDQKFYNFVVIHARADEQVALRIREK
              .* **. :*:*.*  .*:*  * .*.: :******:*******::***:***

TICAM-1.hu    LEALGVPDGATFCEDFQVPGRGELSCLQDAIDHSAFIILLLTSNFDCRLSLHQVNQAMMS
TICAM-1.mu    LETLGVPDGATFCEEFQVPGRGELHCLQDAIDHSGFTILLLTASFDCSLSLHQINHALMN
              **:***********:********* *********.* *****.*** *****:*:*:*.

TICAM-1.hu    NLTRQGSPDCVIPFLPLESSPAQLSSDTASLLSGLVRLDEHSQIFARKVANTFKPHRLQA
TICAM-1.mu    SLTQSGRQDCVIPLLPLECSQAQLSPDTTRLLHSIVWLDEHSPIFARKVANTFKTQKLQA
              .**:.* *****.****.* ****.**  **: :* ***** ***********.::***

TICAM-1.hu    RKAMWRKEQDTRALREQSQHLDGERMQAAALNAAYSAYLQSYLSYQAQMEQLQVAFGSHM
TICAM-1.mu    QRVRWKKAQEARTLKEQSIQLEAERQNVAAISAAYTAYVHSYRAWQAEMNKLGVAFGKNL
              :: *:* *::*:*:*** :**  .**: ***:***:**::**:* * ***.:* ****.::

TICAM-1.hu    SFGTGAPYGARMPFGGQVPLGAPPPFPTWPGCPQPPPLHAWQAGTPPPPSPQPAAFPQS-
TICAM-1.mu    SLGTPTPSWPGCPQP--IPSHPQGGTPVFPYSPQPPSFPQPPCFPQPPSFPQPPSFPLPP
              *:** :* . *  :* .  *:.  .****.:   .. **. ***.:**.

TICAM-1.hu    LPFPQSPAFPTASPAPPQSPGLQPLIIHHAQMVQLGLNNHMWNQRGSQAPEDKTQEAE--
TICAM-1.mu    VSSPQSQSFPSASSPAPQTPGPQPLIIHHAQMVQLGVNNHMWGHTGAQSSDDKTECSENP
              :. *** :**:**.:****. *.******************:*.******. *:*:: ***  :*

TICAM-1.hu    ------------------
TICAM-1.mu    CMGPLTDQGEPLLETPE
```

FIG. 6

```
                  BOX1                                                              BOX2
TICAM-1(TIR).hu   FYNFVILHARADEHIALRVREKLEALGVPDGATFCEDFQVPGRGELSCLQDAIDHSAFI-
TICAM-1(TIR).mu   FYNFVVIHARADEQVALRIREKLETLGVPDGATFCEEFQVPGRGELHCLQDAIDHSGFT-
Mal(TIR).hu       DYDVCVCHSEEDLVAAQDLVSYLEGSTASLRCFLQLRDATPGGAIVSELCQALSSSHCR-
MyD88(TIR).hu     RFDAFICYCPSDIQFVQEMIRQLEQTNYRLKLCVSDRDVLPG-TCVWSIASELIEKRCRR
                   ::  : : :      *           **              . **       .   .

TICAM-1(TIR).hu   -ILLLTSNFDCRLSLHQVNQAMMSNLTRQGSPDCVIPFLPLESSPAQLSSDTASLLSGLV
TICAM-1(TIR).mu   -ILLLTASFDCSLSLHQINHALMNSLTQSGRQDCVIPLLPLECSQAQLSPDTTRLLHSIV
Mal(TIR).hu       -VLLITPGFLQDPWCKYQMLQALTEAP--GAEGCTIPLLSGLSRAAYPPELRFMYYVDGR
MyD88(TIR).hu     MVVVVSDDYLQSKECDFQTKFALSLSPG-AHQKRLIPIKYKAMKKEFPSILRFITVCDYT
                   :::.  .                       .   *:  .           **:.

BOX3
TICAM-1(TIR).hu   RLDEHSQIFARKVANTFKPHR-------------
TICAM-1(TIR).mu   WLDEHSPIFARKVANTFKTQK-------------
Mal(TIR).hu       GPDGGFRQVKEAVMRC------------------
MyD88(TIR).hu     NPCTKSWFWTRLAKALSLP---------------
```

FIG. 12 (a)    Interferon β
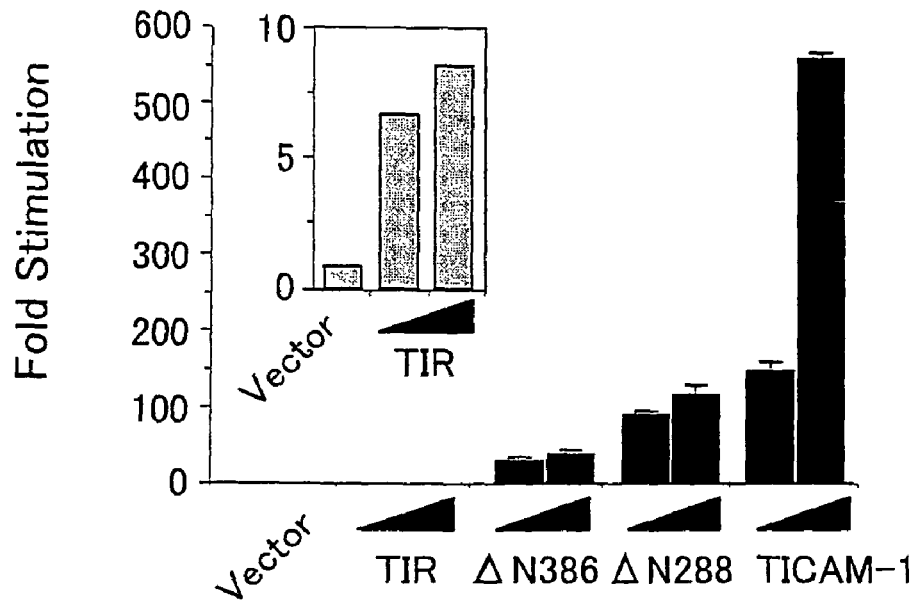
FIG. 12 (b)    NF-κB
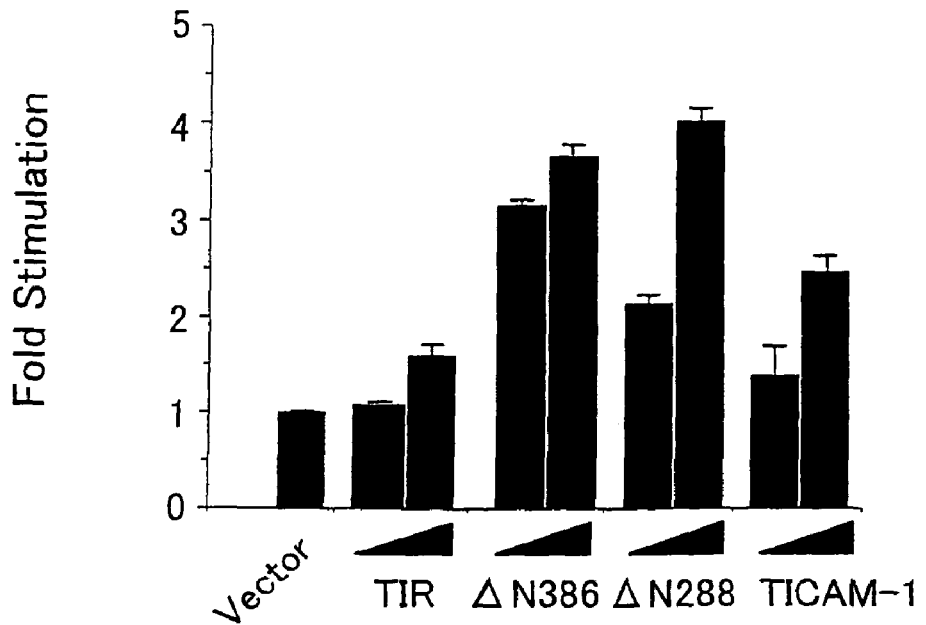

WB : Anti-HA

SEQUENCE LISTING

<160> NUMBER OF SEQ ID NOS: 12

<210> SEQ ID NO 1
<211> LENGTH: 2460
<212> TYPE: DNA
<213> ORGANISM: Homo sapiens US 8,029,778 B2
31                                           32
-continued

```
<220> FEATURE:
<221> NAME/KEY: CDS
<222> LOCATION: (63)..(2198)

<400> SEQUENCE: 1
gtgtggaaca tgccttcacc acctccagct tctgctgccg gaggctgcac ccacctgtgc         60 cc atg gcc tgc aca ggc cca tca ctt cct agc gcc ttc gac att cta         107
   Met Ala Cys Thr Gly Pro Ser Leu Pro Ser Ala Phe Asp Ile Leu
   1               5                   10                  15 ggt gca gca ggc cag gac aag ctc ttg tat ctg aag cac aaa ctg aag         155
Gly Ala Ala Gly Gln Asp Lys Leu Leu Tyr Leu Lys His Lys Leu Lys
                20                  25                  30 acc cca cgc cca ggc tgc cag ggg cag gac ctc ctg cat gcc atg gtt         203
Thr Pro Arg Pro Gly Cys Gln Gly Gln Asp Leu Leu His Ala Met Val
            35                  40                  45 ctc ctg aag ctg ggc cag gaa act gag gcc agg atc tct cta gag gca         251
Leu Leu Lys Leu Gly Gln Glu Thr Glu Ala Arg Ile Ser Leu Glu Ala
        50                  55                  60 ttg aag gcc gat gcg gtg gcc cgg ctg gtg gcc cgc cag tgg gct ggc         299
Leu Lys Ala Asp Ala Val Ala Arg Leu Val Ala Arg Gln Trp Ala Gly
    65                  70                  75 gtg gac agc acc gag gac cca gag gag ccc cca gat gtg tcc tgg gct         347
Val Asp Ser Thr Glu Asp Pro Glu Glu Pro Pro Asp Val Ser Trp Ala
80                  85                  90                  95 gtg gcc cgc ttg tac cac ctg ctg gct gag gag aag ctg tgc ccc gcc         395
Val Ala Arg Leu Tyr His Leu Leu Ala Glu Glu Lys Leu Cys Pro Ala
                100                 105                 110 tcg ctg cgg gac gtg gcc tac cag gaa gcc gtc cgc acc ctc agc tcc         443
Ser Leu Arg Asp Val Ala Tyr Gln Glu Ala Val Arg Thr Leu Ser Ser
            115                 120                 125 agg gac gac cac cgg ctg ggg gaa ctt cag gat gag gcc cga aac cgg         491
Arg Asp Asp His Arg Leu Gly Glu Leu Gln Asp Glu Ala Arg Asn Arg
        130                 135                 140 tgt ggg tgg gac att gct ggg gat cca ggg agc atc cgg acg ctc cag         539
Cys Gly Trp Asp Ile Ala Gly Asp Pro Gly Ser Ile Arg Thr Leu Gln
    145                 150                 155 tcc aat ctg ggc tgc ctc cca cca tcc tcg gct ttg ccc tct ggg acc         587
Ser Asn Leu Gly Cys Leu Pro Pro Ser Ser Ala Leu Pro Ser Gly Thr
160                 165                 170                 175 agg agc ctc cca cgc ccc att gac ggt gtt tcg gac tgg agc caa ggg         635
Arg Ser Leu Pro Arg Pro Ile Asp Gly Val Ser Asp Trp Ser Gln Gly
                180                 185                 190 tgc tcc ctg cga tcc act ggc agc cct gcc tcc ctg gcc agc aac ttg         683
Cys Ser Leu Arg Ser Thr Gly Ser Pro Ala Ser Leu Ala Ser Asn Leu
            195                 200                 205 gaa atc agc cag tcc cct acc atg ccc ttc ctc agc ctg cac cgc agc         731
Glu Ile Ser Gln Ser Pro Thr Met Pro Phe Leu Ser Leu His Arg Ser
        210                 215                 220 cca cat ggg ccc agc aag ctc tgt gac gac ccc cag gcc agc ttg gtg         779
Pro His Gly Pro Ser Lys Leu Cys Asp Asp Pro Gln Ala Ser Leu Val
    225                 230                 235 ccc gag cct gtc ccc ggt ggc tgc cag gag cct gag gag atg agc tgg         827
Pro Glu Pro Val Pro Gly Gly Cys Gln Glu Pro Glu Glu Met Ser Trp
240                 245                 250                 255 ccg cca tcg ggg gag att gcc agc cca cca gag ctg cca agc agc cca         875
Pro Pro Ser Gly Glu Ile Ala Ser Pro Pro Glu Leu Pro Ser Ser Pro
                260                 265                 270 cct cct ggg ctt ccc gaa gtg gcc cca gat gca acc tcc act ggc ctc         923
Pro Pro Gly Leu Pro Glu Val Ala Pro Asp Ala Thr Ser Thr Gly Leu
            275                 280                 285
```

-continued

| | | |
|---|---|---|
| cct gat acc ccc gca gct cca gaa acc agc acc aac tac cca gtg gag<br>Pro Asp Thr Pro Ala Ala Pro Glu Thr Ser Thr Asn Tyr Pro Val Glu<br>290                          295                        300 | | 971 |
| tgc acc gag ggg tct gca ggc ccc cag tct ctc ccc ttg cct att ctg<br>Cys Thr Glu Gly Ser Ala Gly Pro Gln Ser Leu Pro Leu Pro Ile Leu<br>305                          310                        315 | | 1019 |
| gag ccg gtc aaa aac ccc tgc tct gtc aaa gac cag acg cca ctc caa<br>Glu Pro Val Lys Asn Pro Cys Ser Val Lys Asp Gln Thr Pro Leu Gln<br>320                        325                        330                        335 | | 1067 |
| ctt tct gta gaa gat acc acc tct cca aat acc aag ccg tgc cca cct<br>Leu Ser Val Glu Asp Thr Thr Ser Pro Asn Thr Lys Pro Cys Pro Pro<br>340                        345                        350 | | 1115 |
| act ccc acc acc cca gaa aca tcc cct cct cct cct cct cct cct<br>Thr Pro Thr Thr Pro Glu Thr Ser Pro Pro Pro Pro Pro Pro Pro<br>355                        360                        365 | | 1163 |
| tca tct act cct tgt tca gct cac ctg acc ccc tcc ctg ttc cct<br>Ser Ser Thr Pro Cys Ser Ala His Leu Thr Pro Ser Ser Leu Phe Pro<br>370                        375                        380 | | 1211 |
| tcc tcc ctg gaa tca tca tcg gaa cag aaa ttc tat aac ttt gtg atc<br>Ser Ser Leu Glu Ser Ser Ser Glu Gln Lys Phe Tyr Asn Phe Val Ile<br>385                        390                        395 | | 1259 |
| ctc cac gcc agg gca gac gaa cac atc gcc ctg cgg gtt cgg gag aag<br>Leu His Ala Arg Ala Asp Glu His Ile Ala Leu Arg Val Arg Glu Lys<br>400                        405                        410                        415 | | 1307 |
| ctg gag gcc ctt ggc gtg ccc gac ggg gcc acc ttc tgc gag gat ttc<br>Leu Glu Ala Leu Gly Val Pro Asp Gly Ala Thr Phe Cys Glu Asp Phe<br>420                        425                        430 | | 1355 |
| cag gtg ccg ggg cgc ggg gag ctg agc tgc ctg cag gac gcc ata gac<br>Gln Val Pro Gly Arg Gly Glu Leu Ser Cys Leu Gln Asp Ala Ile Asp<br>435                        440                        445 | | 1403 |
| cac tca gct ttc atc atc cta ctt ctc acc tcc aac ttc gac tgt cgc<br>His Ser Ala Phe Ile Ile Leu Leu Leu Thr Ser Asn Phe Asp Cys Arg<br>450                        455                        460 | | 1451 |
| ctg agc ctg cac cag gtg aac caa gcc atg atg agc aac ctc acg cga<br>Leu Ser Leu His Gln Val Asn Gln Ala Met Met Ser Asn Leu Thr Arg<br>465                        470                        475 | | 1499 |
| cag ggg tcg cca gac tgt gtc atc ccc ttc ctg ccc ctg gag agc tcc<br>Gln Gly Ser Pro Asp Cys Val Ile Pro Phe Leu Pro Leu Glu Ser Ser<br>480                        485                        490                        495 | | 1547 |
| ccg gcc cag ctc agc tcc gac acg gcc agc ctc ctc tcc ggg ctg gtg<br>Pro Ala Gln Leu Ser Ser Asp Thr Ala Ser Leu Leu Ser Gly Leu Val<br>500                        505                        510 | | 1595 |
| cgg ctg gac gaa cac tcc cag atc ttc gcc agg aag gtg gcc aac acc<br>Arg Leu Asp Glu His Ser Gln Ile Phe Ala Arg Lys Val Ala Asn Thr<br>515                        520                        525 | | 1643 |
| ttc aag ccc cac agg ctt cag gcc cga aag gcc atg tgg agg aag gaa<br>Phe Lys Pro His Arg Leu Gln Ala Arg Lys Ala Met Trp Arg Lys Glu<br>530                        535                        540 | | 1691 |
| cag gac acc cga gcc ctg cgg gaa cag agc caa cac ctg gac ggt gag<br>Gln Asp Thr Arg Ala Leu Arg Glu Gln Ser Gln His Leu Asp Gly Glu<br>545                        550                        555 | | 1739 |
| cgg atg cag gcg gcg gca ctg aac gca gcc tac tca gcc tac ctc cag<br>Arg Met Gln Ala Ala Ala Leu Asn Ala Ala Tyr Ser Ala Tyr Leu Gln<br>560                        565                        570                        575 | | 1787 |
| agc tac ttg tcc tac cag gca cag atg gag cag ctc cag gtg gct ttt<br>Ser Tyr Leu Ser Tyr Gln Ala Gln Met Glu Gln Leu Gln Val Ala Phe<br>580                        585                        590 | | 1835 |
| ggg agc cac atg tca ttt ggg act ggg gcg ccc tat ggg gct cga atg<br>Gly Ser His Met Ser Phe Gly Thr Gly Ala Pro Tyr Gly Ala Arg Met<br>595                        600                        605 | | 1883 |

```
ccc ttt ggg ggc cag gtg ccc ctg gga gcc ccg cca ccc ttt ccc act       1931
Pro Phe Gly Gly Gln Val Pro Leu Gly Ala Pro Pro Pro Phe Pro Thr
        610                 615                 620 tgg ccg ggg tgc ccg cag ccg cca ccc ctg cac gca tgg cag gct ggc       1979
Trp Pro Gly Cys Pro Gln Pro Pro Pro Leu His Ala Trp Gln Ala Gly
625                 630                 635 acc ccc cca ccg ccc tcc cca cag cca gca gcc ttt cca cag tca ctg       2027
Thr Pro Pro Pro Pro Ser Pro Gln Pro Ala Ala Phe Pro Gln Ser Leu
640                 645                 650                 655 ccc ttc ccg cag tcc cca gcc ttc cct acg gcc tca ccc gca ccc cct       2075
Pro Phe Pro Gln Ser Pro Ala Phe Pro Thr Ala Ser Pro Ala Pro Pro
            660                 665                 670 cag agc cca ggg ctg caa ccc ctc att atc cac cac gca cag atg gta       2123
Gln Ser Pro Gly Leu Gln Pro Leu Ile Ile His His Ala Gln Met Val
            675                 680                 685 cag ctg ggg ctg aac aac cac atg tgg aac cag aga ggg tcc cag gcg       2171
Gln Leu Gly Leu Asn Asn His Met Trp Asn Gln Arg Gly Ser Gln Ala
            690                 695                 700 ccc gag gac aag acg cag gag gca gaa tgaccgcgtg tccttgcctg             2218
Pro Glu Asp Lys Thr Gln Glu Ala Glu
705                 710 accacctggg gaacacccct ggacccaggc atcggccagg accccataga gcaccccggt    2278
ctgccctgtg ccctgtggac agtggaagat gaggtcatct gccactttca ggacattgtc    2338
cgggagccct tcatttagga caaaacgggc gcgatgatgc cctggctttc agggtggtca    2398
gaactggata cggtgtttac aattccaatc tctctatttc tgggtgaagg gtcttggtgg    2458
tg                                                                    2460

<210> SEQ ID NO 2
<211> LENGTH: 712
<212> TYPE: PRT
<213> ORGANISM: Homo sapiens

<400> SEQUENCE: 2

Met Ala Cys Thr Gly Pro Ser Leu Pro Ser Ala Phe Asp Ile Leu Gly
1               5                   10                  15

Ala Ala Gly Gln Asp Lys Leu Leu Tyr Leu Lys His Lys Leu Lys Thr
            20                  25                  30

Pro Arg Pro Gly Cys Gln Gly Gln Asp Leu Leu His Ala Met Val Leu
        35                  40                  45

Leu Lys Leu Gly Gln Glu Thr Glu Ala Arg Ile Ser Leu Glu Ala Leu
    50                  55                  60

Lys Ala Asp Ala Val Ala Arg Leu Val Ala Arg Gln Trp Ala Gly Val
65                  70                  75                  80

Asp Ser Thr Glu Asp Pro Glu Glu Pro Pro Asp Val Ser Trp Ala Val
                85                  90                  95

Ala Arg Leu Tyr His Leu Leu Ala Glu Glu Lys Leu Cys Pro Ala Ser
            100                 105                 110

Leu Arg Asp Val Ala Tyr Gln Glu Ala Val Arg Thr Leu Ser Ser Arg
        115                 120                 125

Asp Asp His Arg Leu Gly Glu Leu Gln Asp Glu Ala Arg Asn Arg Cys
    130                 135                 140

Gly Trp Asp Ile Ala Gly Asp Pro Gly Ser Ile Arg Thr Leu Gln Ser
145                 150                 155                 160

Asn Leu Gly Cys Leu Pro Pro Ser Ser Ala Leu Pro Ser Gly Thr Arg
                165                 170                 175

Ser Leu Pro Arg Pro Ile Asp Gly Val Ser Asp Trp Ser Gln Gly Cys
```

```
                    180                 185                 190
Ser Leu Arg Ser Thr Gly Ser Pro Ala Ser Leu Ala Ser Asn Leu Glu
                195                 200                 205

Ile Ser Gln Ser Pro Thr Met Pro Phe Leu Ser Leu His Arg Ser Pro
            210                 215                 220

His Gly Pro Ser Lys Leu Cys Asp Asp Pro Gln Ala Ser Leu Val Pro
225                 230                 235                 240

Glu Pro Val Pro Gly Gly Cys Gln Glu Pro Glu Met Ser Trp Pro
                245                 250                 255

Pro Ser Gly Glu Ile Ala Ser Pro Glu Leu Pro Ser Ser Pro Pro
            260                 265                 270

Pro Gly Leu Pro Glu Val Ala Pro Asp Ala Thr Ser Thr Gly Leu Pro
            275                 280                 285

Asp Thr Pro Ala Ala Pro Glu Thr Ser Thr Asn Tyr Pro Val Glu Cys
        290                 295                 300

Thr Glu Gly Ser Ala Gly Pro Gln Ser Leu Pro Leu Pro Ile Leu Glu
305                 310                 315                 320

Pro Val Lys Asn Pro Cys Ser Val Lys Asp Gln Thr Pro Leu Gln Leu
                325                 330                 335

Ser Val Glu Asp Thr Thr Ser Pro Asn Thr Lys Pro Cys Pro Pro Thr
            340                 345                 350

Pro Thr Thr Pro Glu Thr Ser Pro Pro Pro Pro Pro Pro Pro Ser
            355                 360                 365

Ser Thr Pro Cys Ser Ala His Leu Thr Pro Ser Ser Leu Phe Pro Ser
        370                 375                 380

Ser Leu Glu Ser Ser Glu Gln Lys Phe Tyr Asn Phe Val Ile Leu
385                 390                 395                 400

His Ala Arg Ala Asp Glu His Ile Ala Leu Arg Val Arg Glu Lys Leu
                405                 410                 415

Glu Ala Leu Gly Val Pro Asp Gly Ala Thr Phe Cys Glu Asp Phe Gln
            420                 425                 430

Val Pro Gly Arg Gly Glu Leu Ser Cys Leu Gln Asp Ala Ile Asp His
            435                 440                 445

Ser Ala Phe Ile Ile Leu Leu Leu Thr Ser Asn Phe Asp Cys Arg Leu
        450                 455                 460

Ser Leu His Gln Val Asn Gln Ala Met Met Ser Asn Leu Thr Arg Gln
465                 470                 475                 480

Gly Ser Pro Asp Cys Val Ile Pro Phe Leu Pro Leu Glu Ser Ser Pro
                485                 490                 495

Ala Gln Leu Ser Ser Asp Thr Ala Ser Leu Leu Ser Gly Leu Val Arg
            500                 505                 510

Leu Asp Glu His Ser Gln Ile Phe Ala Arg Lys Val Ala Asn Thr Phe
            515                 520                 525

Lys Pro His Arg Leu Gln Ala Arg Lys Ala Met Trp Arg Lys Glu Gln
            530                 535                 540

Asp Thr Arg Ala Leu Arg Glu Gln Ser Gln His Leu Asp Gly Glu Arg
545                 550                 555                 560

Met Gln Ala Ala Ala Leu Asn Ala Ala Tyr Ser Ala Tyr Leu Gln Ser
                565                 570                 575

Tyr Leu Ser Tyr Gln Ala Gln Met Glu Gln Leu Gln Val Ala Phe Gly
            580                 585                 590

Ser His Met Ser Phe Gly Thr Gly Ala Pro Tyr Gly Ala Arg Met Pro
            595                 600                 605
```

```
Phe Gly Gly Gln Val Pro Leu Gly Ala Pro Pro Phe Pro Thr Trp
610             615                 620

Pro Gly Cys Pro Gln Pro Pro Leu His Ala Trp Gln Ala Gly Thr
625             630                 635                 640

Pro Pro Pro Ser Pro Gln Pro Ala Ala Phe Pro Gln Ser Leu Pro
            645                 650                 655

Phe Pro Gln Ser Pro Ala Phe Pro Thr Ala Ser Pro Ala Pro Pro Gln
                660                 665                 670

Ser Pro Gly Leu Gln Pro Leu Ile Ile His His Ala Gln Met Val Gln
        675                 680                 685

Leu Gly Leu Asn Asn His Met Trp Asn Gln Arg Gly Ser Gln Ala Pro
    690                 695                 700

Glu Asp Lys Thr Gln Glu Ala Glu
705                 710

<210> SEQ ID NO 3
<211> LENGTH: 2299
<212> TYPE: DNA
<213> ORGANISM: Mus musculus
<220> FEATURE:
<221> NAME/KEY: CDS
<222> LOCATION: (66)..(2261)

<400> SEQUENCE: 3
tcggttcgga acatgtctcc acccacccca ccctctgtgg ctccaggctt cattctcccc       60 catcc atg gat aac cca ggg cct tcg ctc cgt ggt gcc ttt ggc att cta     110
      Met Asp Asn Pro Gly Pro Ser Leu Arg Gly Ala Phe Gly Ile Leu
      1               5                   10                  15 ggt gcc ttg gaa agg gac agg ctg acc cac ctg aaa cac aag ctg ggg       158
Gly Ala Leu Glu Arg Asp Arg Leu Thr His Leu Lys His Lys Leu Gly
                20                  25                  30 agt ctg tgt tca ggc agc cag gag tca aag ctt ctc cat gcc atg gta       206
Ser Leu Cys Ser Gly Ser Gln Glu Ser Lys Leu Leu His Ala Met Val
            35                  40                  45 ctc ctg gct ctg ggc cag gac acg gag gcc agg gtc tct ctg gag tcc       254
Leu Leu Ala Leu Gly Gln Asp Thr Glu Ala Arg Val Ser Leu Glu Ser
        50                  55                  60 ttg aag atg aac aca gta gcc cag ctg gta gcc cac cag tgg gca gac       302
Leu Lys Met Asn Thr Val Ala Gln Leu Val Ala His Gln Trp Ala Asp
    65                  70                  75 atg gag acc aca gag ggc cct gag gag cct cca gac ttg tcc tgg acg       350
Met Glu Thr Thr Glu Gly Pro Glu Glu Pro Pro Asp Leu Ser Trp Thr
80                  85                  90                  95 gtg gct cgc ctg tac cac ctg ctg gct gag gag aac ctg tgt ccg gcc       398
Val Ala Arg Leu Tyr His Leu Leu Ala Glu Glu Asn Leu Cys Pro Ala
                100                 105                 110 tcc aca agg gac atg gct tac cag gtg gcc ctt cgt gac ttt gcc tcc       446
Ser Thr Arg Asp Met Ala Tyr Gln Val Ala Leu Arg Asp Phe Ala Ser
            115                 120                 125 cag ggt gac cac cag ctg ggc caa ctc cag aat gag gcc tgg gat cgg       494
Gln Gly Asp His Gln Leu Gly Gln Leu Gln Asn Glu Ala Trp Asp Arg
        130                 135                 140 tgc agt tca gat atc aag ggg gac ccc agt ggt ttc cag cca ctc cat       542
Cys Ser Ser Asp Ile Lys Gly Asp Pro Ser Gly Phe Gln Pro Leu His
    145                 150                 155 tct cat cag ggt tcc ctg cag cca cct tca gca tcc cct gca gtg acc       590
Ser His Gln Gly Ser Leu Gln Pro Pro Ser Ala Ser Pro Ala Val Thr
160                 165                 170                 175 aga agc cag cct cgt ccc att gac aca cca gac tgg agt tgg gga cat       638
Arg Ser Gln Pro Arg Pro Ile Asp Thr Pro Asp Trp Ser Trp Gly His
```

-continued

```
                  180                 185                 190
acg tta cac tcc acc aac agc act gcc tca ctg gcc agc cac cta gag      686
Thr Leu His Ser Thr Asn Ser Thr Ala Ser Leu Ala Ser His Leu Glu
            195                 200                 205 atc agc cag tca ccc act ctt gcc ttt ctc tct tca cac cat gga acc      734
Ile Ser Gln Ser Pro Thr Leu Ala Phe Leu Ser Ser His His Gly Thr
        210                 215                 220 cat ggg ccc agc aag cta tgt aac aca ccg ctg gac act cag gag cct      782
His Gly Pro Ser Lys Leu Cys Asn Thr Pro Leu Asp Thr Gln Glu Pro
    225                 230                 235 cag ctt gtc cct gaa ggc tgc caa gaa cct gag gag ata agc tgg cct      830
Gln Leu Val Pro Glu Gly Cys Gln Glu Pro Glu Glu Ile Ser Trp Pro
240                 245                 250                 255 cca tca gtg gag acc agt gtc tcc tta ggg tta cca cac gaa att agc      878
Pro Ser Val Glu Thr Ser Val Ser Leu Gly Leu Pro His Glu Ile Ser
            260                 265                 270 gtt cca gag gtg tct cca gag gag gct tcg ccc atc ctc cct gac gcc      926
Val Pro Glu Val Ser Pro Glu Glu Ala Ser Pro Ile Leu Pro Asp Ala
        275                 280                 285 ctg gct gct cca gac aca agt gtc cac tgt ccc att gaa tgc aca gag      974
Leu Ala Ala Pro Asp Thr Ser Val His Cys Pro Ile Glu Cys Thr Glu
    290                 295                 300 ttg tct aca aac tcc agg tct ccc ctg acg tcc acc aca gaa agt gtt     1022
Leu Ser Thr Asn Ser Arg Ser Pro Leu Thr Ser Thr Thr Glu Ser Val
305                 310                 315 gga aag cag tgg cct att aca agt cag agg tca cct cag gtt cct gta     1070
Gly Lys Gln Trp Pro Ile Thr Ser Gln Arg Ser Pro Gln Val Pro Val
320                 325                 330                 335 gga gat gat tct ctg cag aac acc acg tca tcc agc cct cct gcc cag     1118
Gly Asp Asp Ser Leu Gln Asn Thr Thr Ser Ser Ser Pro Pro Ala Gln
            340                 345                 350 cca cca tcc ctc caa gcc tcc cct aag ctg cct cct tcc cct ctg tcc     1166
Pro Pro Ser Leu Gln Ala Ser Pro Lys Leu Pro Pro Ser Pro Leu Ser
        355                 360                 365 tct gct tcc tcc ccg agc agc tac cct gct cct cca acc tcc aca tcc     1214
Ser Ala Ser Ser Pro Ser Ser Tyr Pro Ala Pro Pro Thr Ser Thr Ser
    370                 375                 380 cct gtt ttg gac cac tca gaa aca tct gat cag aaa ttc tat aac ttt     1262
Pro Val Leu Asp His Ser Glu Thr Ser Asp Gln Lys Phe Tyr Asn Phe
385                 390                 395 gtg gtt atc cat gcc agg gct gat gaa cag gtg gcc cta cgt att cgg     1310
Val Val Ile His Ala Arg Ala Asp Glu Gln Val Ala Leu Arg Ile Arg
400                 405                 410                 415 gag aag ctg gag acc ctc ggg gta cct gac ggg gcc acc ttc tgt gag     1358
Glu Lys Leu Glu Thr Leu Gly Val Pro Asp Gly Ala Thr Phe Cys Glu
            420                 425                 430 gaa ttt cag gtg ccc ggg cgt ggt gag ctg cac tgt ctc caa gat gcc     1406
Glu Phe Gln Val Pro Gly Arg Gly Glu Leu His Cys Leu Gln Asp Ala
        435                 440                 445 atc gat cac tcg ggg ttc acg atc ctc ctg act gct agc ttt gat         1454
Ile Asp His Ser Gly Phe Thr Ile Leu Leu Thr Ala Ser Phe Asp
    450                 455                 460 tgc agc ctg agc ctg cat caa atc aac cat gct ctc atg aac agc ctt     1502
Cys Ser Leu Ser Leu His Gln Ile Asn His Ala Leu Met Asn Ser Leu
465                 470                 475 aca cag tct ggg agg cag gac tgt gtg atc ccc ctc ctc cca ctt gag     1550
Thr Gln Ser Gly Arg Gln Asp Cys Val Ile Pro Leu Leu Pro Leu Glu
480                 485                 490                 495 tgt tct cag gcc cag ctc agc cca gat aca acc aga ctg ctc cac agc     1598
Cys Ser Gln Ala Gln Leu Ser Pro Asp Thr Thr Arg Leu Leu His Ser
```

| | | | | | | | | | | | | | | | |
|---|---|---|---|---|---|---|---|---|---|---|---|---|---|---|---|
| | | | | 500 | | | | | 505 | | | | | 510 | |
| att | gtg | tgg | ctg | gat | gaa | cac | tcc | cca | atc | ttc | gcc | aga | aag | gtg | gca | 1646 |
| Ile | Val | Trp | Leu | Asp | Glu | His | Ser | Pro | Ile | Phe | Ala | Arg | Lys | Val | Ala |
| | | | | 515 | | | | | 520 | | | | | 525 | |
| aac | acc | ttc | aag | aca | cag | aag | ctc | cag | gca | cag | cgg | gta | cgc | tgg | aag | 1694 |
| Asn | Thr | Phe | Lys | Thr | Gln | Lys | Leu | Gln | Ala | Gln | Arg | Val | Arg | Trp | Lys |
| | | | | 530 | | | | | 535 | | | | | 540 | |
| aaa | gcg | cag | gag | gcc | aga | acc | ctc | aag | gag | cag | agc | ata | cag | ctg | gag | 1742 |
| Lys | Ala | Gln | Glu | Ala | Arg | Thr | Leu | Lys | Glu | Gln | Ser | Ile | Gln | Leu | Glu |
| | | | | 545 | | | | | 550 | | | | | 555 | |
| gca | gag | cgg | caa | aac | gtg | gca | gcc | ata | tct | gct | gcc | tac | aca | gcc | tat | 1790 |
| Ala | Glu | Arg | Gln | Asn | Val | Ala | Ala | Ile | Ser | Ala | Ala | Tyr | Thr | Ala | Tyr |
| 560 | | | | | 565 | | | | | 570 | | | | | 575 |
| gtc | cat | agc | tat | agg | gcc | tgg | caa | gca | gag | atg | aac | aaa | ctt | ggg | gtg | 1838 |
| Val | His | Ser | Tyr | Arg | Ala | Trp | Gln | Ala | Glu | Met | Asn | Lys | Leu | Gly | Val |
| | | | | 580 | | | | | 585 | | | | | 590 | |
| gct | ttt | ggg | aag | aac | ttg | tca | ctg | ggg | act | cca | aca | ccc | agc | tgg | ccc | 1886 |
| Ala | Phe | Gly | Lys | Asn | Leu | Ser | Leu | Gly | Thr | Pro | Thr | Pro | Ser | Trp | Pro |
| | | | | 595 | | | | | 600 | | | | | 605 | |
| gga | tgt | cca | cag | cca | ata | cct | tct | cat | cct | cag | ggt | ggt | act | cca | gtt | 1934 |
| Gly | Cys | Pro | Gln | Pro | Ile | Pro | Ser | His | Pro | Gln | Gly | Gly | Thr | Pro | Val |
| | | | | 610 | | | | | 615 | | | | | 620 | |
| ttc | ccc | tat | tcc | cca | cag | cct | cca | tcc | ttc | cct | cag | cct | cca | tgc | ttc | 1982 |
| Phe | Pro | Tyr | Ser | Pro | Gln | Pro | Pro | Ser | Phe | Pro | Gln | Pro | Pro | Cys | Phe |
| | | | | 625 | | | | | 630 | | | | | 635 | |
| cct | cag | cct | cca | tcc | ttc | cct | cag | cct | cca | tcc | ttc | cca | ctg | cct | cca | 2030 |
| Pro | Gln | Pro | Pro | Ser | Phe | Pro | Gln | Pro | Pro | Ser | Phe | Pro | Leu | Pro | Pro |
| 640 | | | | | 645 | | | | | 650 | | | | | 655 |
| gtc | tct | tcc | cca | cag | tcc | caa | tcc | ttt | cca | tca | gcc | tcc | tcc | cca | gcc | 2078 |
| Val | Ser | Ser | Pro | Gln | Ser | Gln | Ser | Phe | Pro | Ser | Ala | Ser | Ser | Pro | Ala |
| | | | | 660 | | | | | 665 | | | | | 670 | |
| cca | cag | act | cca | gga | cct | cag | cct | ctc | att | att | cac | cat | gcc | cag | atg | 2126 |
| Pro | Gln | Thr | Pro | Gly | Pro | Gln | Pro | Leu | Ile | Ile | His | His | Ala | Gln | Met |
| | | | | 675 | | | | | 680 | | | | | 685 | |
| gtt | cag | ctg | ggt | gtc | aac | aat | cac | atg | tgg | ggc | cac | aca | ggg | gcc | cag | 2174 |
| Val | Gln | Leu | Gly | Val | Asn | Asn | His | Met | Trp | Gly | His | Thr | Gly | Ala | Gln |
| | | | | 690 | | | | | 695 | | | | | 700 | |
| tca | tct | gat | gac | aag | act | gag | tgt | tcg | gag | aac | ccc | tgt | atg | ggc | cct | 2222 |
| Ser | Ser | Asp | Asp | Lys | Thr | Glu | Cys | Ser | Glu | Asn | Pro | Cys | Met | Gly | Pro |
| 705 | | | | | 710 | | | | | 715 | | | | | | |
| ctg | act | gat | cag | ggc | gaa | ccc | ctt | ctt | gag | act | cca | gag | tgaccaggtt | | | 2271 |
| Leu | Thr | Asp | Gln | Gly | Glu | Pro | Leu | Leu | Glu | Thr | Pro | Glu | | | |
| 720 | | | | 725 | | | | | 730 | | | | | | | ggacccacc tagatggcta gagtgaca 2299

<210> SEQ ID NO 4
<211> LENGTH: 732
<212> TYPE: PRT
<213> ORGANISM: Mus musculus

<400> SEQUENCE: 4

Met Asp Asn Pro Gly Pro Ser Leu Arg Gly Ala Phe Gly Ile Leu Gly
1               5                   10                  15

Ala Leu Glu Arg Asp Arg Leu Thr His Leu Lys His Lys Leu Gly Ser
            20                  25                  30

Leu Cys Ser Gly Ser Gln Glu Ser Lys Leu Leu His Ala Met Val Leu
        35                  40                  45

Leu Ala Leu Gly Gln Asp Thr Glu Ala Arg Val Ser Leu Glu Ser Leu
    50                  55                  60

```
Lys Met Asn Thr Val Ala Gln Leu Val Ala His Gln Trp Ala Asp Met
 65                  70                  75                  80

Glu Thr Thr Glu Gly Pro Glu Pro Pro Asp Leu Ser Trp Thr Val
                 85                  90                  95

Ala Arg Leu Tyr His Leu Leu Ala Glu Glu Asn Leu Cys Pro Ala Ser
                100                 105                 110

Thr Arg Asp Met Ala Tyr Gln Val Ala Leu Arg Asp Phe Ala Ser Gln
            115                 120                 125

Gly Asp His Gln Leu Gly Leu Gln Asn Glu Ala Trp Asp Arg Cys
130                 135                 140

Ser Ser Asp Ile Lys Gly Asp Pro Ser Gly Phe Gln Pro Leu His Ser
145                 150                 155                 160

His Gln Gly Ser Leu Gln Pro Pro Ser Ala Ser Pro Ala Val Thr Arg
                165                 170                 175

Ser Gln Pro Arg Pro Ile Asp Thr Pro Asp Trp Ser Trp Gly His Thr
            180                 185                 190

Leu His Ser Thr Asn Ser Thr Ala Ser Leu Ala Ser His Leu Glu Ile
        195                 200                 205

Ser Gln Ser Pro Thr Leu Ala Phe Leu Ser Ser His His Gly Thr His
210                 215                 220

Gly Pro Ser Lys Leu Cys Asn Thr Pro Leu Asp Thr Gln Glu Pro Gln
225                 230                 235                 240

Leu Val Pro Glu Gly Cys Gln Glu Pro Glu Glu Ile Ser Trp Pro Pro
                245                 250                 255

Ser Val Glu Thr Ser Val Ser Leu Gly Leu Pro His Glu Ile Ser Val
            260                 265                 270

Pro Glu Val Ser Pro Glu Glu Ala Ser Pro Ile Leu Pro Asp Ala Leu
        275                 280                 285

Ala Ala Pro Asp Thr Ser Val His Cys Pro Ile Glu Cys Thr Glu Leu
    290                 295                 300

Ser Thr Asn Ser Arg Ser Pro Leu Thr Ser Thr Thr Glu Ser Val Gly
305                 310                 315                 320

Lys Gln Trp Pro Ile Thr Ser Gln Arg Ser Pro Gln Val Pro Val Gly
                325                 330                 335

Asp Asp Ser Leu Gln Asn Thr Thr Ser Ser Ser Pro Pro Ala Gln Pro
            340                 345                 350

Pro Ser Leu Gln Ala Ser Pro Lys Leu Pro Pro Ser Pro Leu Ser Ser
        355                 360                 365

Ala Ser Ser Pro Ser Ser Tyr Pro Ala Pro Pro Thr Ser Thr Ser Pro
    370                 375                 380

Val Leu Asp His Ser Glu Thr Ser Asp Gln Lys Phe Tyr Asn Phe Val
385                 390                 395                 400

Val Ile His Ala Arg Ala Asp Glu Gln Val Ala Leu Arg Ile Arg Glu
                405                 410                 415

Lys Leu Glu Thr Leu Gly Val Pro Asp Gly Ala Thr Phe Cys Glu Glu
            420                 425                 430

Phe Gln Val Pro Gly Arg Gly Glu Leu His Cys Leu Gln Asp Ala Ile
        435                 440                 445

Asp His Ser Gly Phe Thr Ile Leu Leu Leu Thr Ala Ser Phe Asp Cys
    450                 455                 460

Ser Leu Ser Leu His Gln Ile Asn His Ala Leu Met Asn Ser Leu Thr
465                 470                 475                 480

Gln Ser Gly Arg Gln Asp Cys Val Ile Pro Leu Leu Pro Leu Glu Cys
                485                 490                 495
```

```
Ser Gln Ala Gln Leu Ser Pro Asp Thr Thr Arg Leu Leu His Ser Ile
            500                 505                 510

Val Trp Leu Asp Glu His Ser Pro Ile Phe Ala Arg Lys Val Ala Asn
            515                 520                 525

Thr Phe Lys Thr Gln Lys Leu Gln Ala Gln Arg Val Arg Trp Lys Lys
530                 535                 540

Ala Gln Glu Ala Arg Thr Leu Lys Glu Gln Ser Ile Gln Leu Glu Ala
545                 550                 555                 560

Glu Arg Gln Asn Val Ala Ala Ile Ser Ala Tyr Thr Ala Tyr Val
                565                 570                 575

His Ser Tyr Arg Ala Trp Gln Ala Glu Met Asn Lys Leu Gly Val Ala
            580                 585                 590

Phe Gly Lys Asn Leu Ser Leu Gly Thr Pro Thr Pro Ser Trp Pro Gly
            595                 600                 605

Cys Pro Gln Pro Ile Pro Ser His Pro Gln Gly Gly Thr Pro Val Phe
            610                 615                 620

Pro Tyr Ser Pro Gln Pro Ser Phe Pro Gln Pro Pro Cys Phe Pro
625                 630                 635                 640

Gln Pro Pro Ser Phe Pro Gln Pro Ser Phe Pro Leu Pro Pro Val
                645                 650                 655

Ser Ser Pro Gln Ser Gln Ser Phe Pro Ser Ala Ser Ser Pro Ala Pro
            660                 665                 670

Gln Thr Pro Gly Pro Gln Pro Leu Ile Ile His His Ala Gln Met Val
            675                 680                 685

Gln Leu Gly Val Asn Asn His Met Trp Gly His Thr Gly Ala Gln Ser
            690                 695                 700

Ser Asp Asp Lys Thr Glu Cys Ser Glu Asn Pro Cys Met Gly Pro Leu
705                 710                 715                 720

Thr Asp Gln Gly Glu Pro Leu Leu Glu Thr Pro Glu
                725                 730

<210> SEQ ID NO 5
<211> LENGTH: 19
<212> TYPE: RNA
<213> ORGANISM: Artificial Sequence
<220> FEATURE:
<223> OTHER INFORMATION: sense strand for RNAi of human TICAM-1

<400> SEQUENCE: 5
gaccagacgc cacuccaac                                               19

<210> SEQ ID NO 6
<211> LENGTH: 19
<212> TYPE: RNA
<213> ORGANISM: Artificial Sequence
<220> FEATURE:
<223> OTHER INFORMATION: antisense strand for RNAi of human TICAM-1

<400> SEQUENCE: 6
guuggagugg cgucugguc                                               19

<210> SEQ ID NO 7
<211> LENGTH: 20
<212> TYPE: DNA
<213> ORGANISM: Artificial Sequence
<220> FEATURE:
<223> OTHER INFORMATION: 5' primer for human TICAM-1

<400> SEQUENCE: 7
```

```
ccagatgcaa cctccactgg                                           20
```

<210> SEQ ID NO 8
<211> LENGTH: 21
<212> TYPE: DNA
<213> ORGANISM: Artificial Sequence
<220> FEATURE:
<223> OTHER INFORMATION: 3' primer for human TICAM-1

<400> SEQUENCE: 8

```
tggaggaagg aacaggacac c                                         21
```

<210> SEQ ID NO 9
<211> LENGTH: 19
<212> TYPE: RNA
<213> ORGANISM: Artificial Sequence
<220> FEATURE:
<223> OTHER INFORMATION: sense strand for RNAi of lamin A/C

<400> SEQUENCE: 9

```
cuggacuucc agaagaaca                                            19
```

<210> SEQ ID NO 10
<211> LENGTH: 19
<212> TYPE: RNA
<213> ORGANISM: Artificial Sequence
<220> FEATURE:
<223> OTHER INFORMATION: antisense strand for RNAi of lamin A/C

<400> SEQUENCE: 10

```
uguucuucug gaaguccag                                            19
```

<210> SEQ ID NO 11
<211> LENGTH: 132
<212> TYPE: PRT
<213> ORGANISM: Homo sapiens

<400> SEQUENCE: 11

```
Asp Tyr Asp Val Cys Val Cys His Ser Glu Glu Asp Leu Val Ala Ala
  1               5                  10                  15

Gln Asp Leu Val Ser Tyr Leu Glu Gly Ser Thr Ala Ser Leu Arg Cys
             20                  25                  30

Phe Leu Gln Leu Arg Asp Ala Thr Pro Gly Gly Ala Ile Val Ser Glu
         35                  40                  45

Leu Cys Gln Ala Leu Ser Ser Ser His Cys Arg Val Leu Leu Ile Thr
     50                  55                  60

Pro Gly Phe Leu Gln Asp Pro Trp Cys Lys Tyr Gln Met Leu Gln Ala
 65                  70                  75                  80

Leu Thr Glu Ala Pro Gly Ala Glu Gly Cys Thr Ile Pro Leu Leu Ser
                 85                  90                  95

Gly Leu Ser Arg Ala Ala Tyr Pro Pro Glu Leu Arg Phe Met Tyr Tyr
            100                 105                 110

Val Asp Gly Arg Gly Pro Asp Gly Gly Phe Arg Gln Val Lys Glu Ala
        115                 120                 125

Val Met Arg Cys
    130
```

<210> SEQ ID NO 12
<211> LENGTH: 137
<212> TYPE: PRT
<213> ORGANISM: Homo sapiens

<400> SEQUENCE: 12

```
Arg Phe Asp Ala Phe Ile Cys Tyr Cys Pro Ser Asp Ile Gln Phe Val
 1               5                  10                  15

Gln Glu Met Ile Arg Gln Leu Glu Gln Thr Asn Tyr Arg Leu Lys Leu
            20                  25                  30

Cys Val Ser Asp Arg Asp Val Leu Pro Gly Thr Cys Val Trp Ser Ile
        35                  40                  45

Ala Ser Glu Leu Ile Glu Lys Arg Cys Arg Arg Met Val Val Val Val
    50                  55                  60

Ser Asp Asp Tyr Leu Gln Ser Lys Glu Cys Asp Phe Gln Thr Lys Phe
65                      70                  75                  80

Ala Leu Ser Leu Ser Pro Gly Ala His Gln Lys Arg Leu Ile Pro Ile
                85                  90                  95

Lys Tyr Lys Ala Met Lys Lys Glu Phe Pro Ser Ile Leu Arg Phe Ile
            100                 105                 110

Thr Val Cys Asp Tyr Thr Asn Pro Cys Thr Lys Ser Trp Phe Trp Thr
    115                 120                 125

Arg Leu Ala Lys Ala Leu Ser Leu Pro
130                 135
```

METHODS OF USING TICAM-1, AN ADAPTER PROTEIN THAT BINDS TOLL-LIKE RECEPTOR 3

RELATED APPLICATIONS

This application is a divisional of application Ser. No. 10/536,802, filed Sep. 22, 2005, now U.S. Pat. No. 7,582,437; which is a U.S. national stage under 35 U.S.C. 371 of Application No. PCT/JP2003/014854, filed Nov. 20, 2003; the contents of which are incorporated by reference herein.

TECHNICAL FIELD

The present invention relates to a novel adaptor protein that can induce production of type I interferon by binding to mammalian Toll-like receptor 3, mutants of the same, and a gene for encoding the same, and use of the same.

BACKGROUND ART

Interferon is a protein, which plays an important role in adaptive immune response against viruses.

Because of its important role in the adaptive immune system, there have been many studies on the role of the interferon in the immune system. However, it has been only limited knowledge on a signaling pathway for in-vivo production of interferon in the immune system responds to pathogens.

After recent discovery of Toll-like receptor (hereinafter just referred to as "TLR" for abbreviation where appropriate) as a receptor that recognize pathogens in mammal innate immune system, researches on TLR are leading to the understanding of the signaling pathway relating to the pathogen recognition in the innate immune system.

The mammalian TLR families, which are principal tissues appearing to be in large part conserved across Drosophila and human, recognize a variety of microbial components and mediate (i) activation of nuclear factor κB (hereinafter just referred to as "NF-κB" for abbreviation) and (ii) other signaling pathways.

For human, 10 receptors (human TLR 1 to 10) belonging to the TLR family have been identified by now and mouse homologue thereof (mouse TLR 1 to 10) have been identified. TLR family proteins is made of (i) an extracellular domain containing a plurality of leucine-rich repeats (LRRs) and a carboxylic terminal (C-terminal) flanking region, and (ii) a cytoplasmic (intercellular) signaling domain. The cytoplasmic signaling domain is called Toll/interleucine-1 receptor homology domain (TIR). Each TLR recognizes one or more distinct ligand(s) with its extracellular domain, and induces immune response(s), presumably via the intercellular TIR. Each TLR induces different, sometimes overlapping immune responses. All TLR family proteins contain a TIR domain in their cytoplasmic region, and most of the TIR domain is considered to be responsible for signaling and interaction with the adaptor molecule MyD88 or Mal/TIRAP. That is, TLR2, TLR4, TLR5, TLR7, and TLR9 transmit signals via the adaptor molecule MyD88 upon agonist stimulation, thereby to activate NF-κB.

Meanwhile, it was reported recently that the adaptor molecule Mal/TIRAP (an adaptor molecule called MyD88-adapter-like or TIRAP), which associates with TLR 4, relates to the signaling pathway via TLR 4, (e.g., refer to Document 1: Kawai et al., Lipopolysaccharide stimulates the MyD88-independent pathway and results in activation of IFN-regulatory factor 3 and the expression of a subset of lipopolysaccharide-inducible genes, J. Immunol. 167: 5887-5894, 2001; Document 2: Horng et al., TIRAP: An adapter molecule in the Toll signaling pathway, Nat. Immunol. 2: 835-841, 2001; and Document 3: Fitzgerald et al., Mal (MyD88-adapter-like) is required for Toll-like receptor-4 signal transduction, Nature 413: 78-83, 2001).

According to the report, TLR 4 is involved in activation of NF-κB, MAPK, and interferon β promoter. This unique ability of TLR 4 to induce the activation of interferon β promoter is ascribed to signaling pathway mediated by the adaptor molecule Mal/TIRAP that binds to TLR 4. This signaling pathway is called "a MyD88-independent pathway". That is, in the signaling via TLR 4, activation of NF-κB and type-I interferon promoter is controlled by cooperation between TLR 4 and the adaptor molecule Mal/TRRAP that is a second adaptor molecule different from the adaptor molecule MyD88.

In Microphages (Mf), STAT1 α/β phosphorylation is induced by the interferon β activation as a result of TLR 4 stimulation, not TLR 2 stimulation. Expression of the gene encoding interferon β subsequently induces production of MCP (Monocyte Chemoattractant Protein)-5, IP (interferon Inductive Protein)-10m, and iNOS (inductive NO synthetic enzyme). Again, this occurs via the MyD88-independent pathway, even in MyD88−/− cell (a cell from which the adaptor molecule MyD88 is deleted).

A current concept considered most likely is that the adaptor molecule Mal/TIRAP covers the MyD88-independent pathway.

In contrast, the inventor of the present invention studied immune responses induced by double-stranded RNA and mediated via human TLR 3, and found that human TLR 3 relates to recognition of double-stranded RNA on a cell surface of human fibroblast, and triggers downstream signaling that induces the interferon β production. (e.g., Document 4: Matsumoto et al., Establishment of a monoclonal antibody against human Toll-like receptor 3 that blocks double-stranded RNA-mediated signaling, Biochem. Biophys. Res. Commun. 293: 1364-1369, electronically published on May 31, 2002). That is, the inventors of the present invention showed that the interferon β promoter activation and interferon β production is rapidly and strongly induced by human TLR 3 in response to double-stranded RNA. Reporter gene assay showed that human TLR3 mediates the interferon β promoter activation, and to a lesser extent the NF-κB activation (c.f. Document 4 for example). This result with respect to TLR3 is quite different from those of TLR, TLR2, TLR5, TLR7, and TL9, which activate NF-κB and p38 MAPK (MAP kinase) through the adaptor molecule MyD88 after recognizing their specific ligands.

The type I interferon (interferon α and interferon β) that TLR 3 induces is known to have anti-virus effect and anti-cancer effect. Specifically, type I interferon has the following effects.

Type I interferon is known to exhibit the anti-virus effect by the following function mechanisms:

1) The type I interferon destabilizes mRNA of a virus and activates intercellular gene that inhibits protein translation of hosts, thereby to inhibit replication and multiplication of the virus;

2) The type I interferon induces expression of MHC class I molecule so as to induce resistance against natural killer (NK) cells. Further, type I interferon enhances sensitivity with respect to CD+8 cytotoxic T cell. In addition, type I interferon participates to inhibition of T cell activation and to T cell suppressor activation; and 3) The type I interferon activates natural killer (NK) cells that selectively damage virus-infected cells, and causes NKcell induced apoptosis in the virus. Moreover, the type I interferon is known to exhibit anti-tumor effect by the following function mechanisms:

1) The type I interferon destabilizes mRNA in tumor cells and activates intercellular gene that inhibits protein translation of hosts. This inhibits protein synthesis in the tumor cells, thereby inhibiting multiplication of the tumor cells;

2) The type I interferon activates anti-tumor effectors such as microphages, NK cells, natural killer T (NKT) cells, and the like. Via damaging of the tumor cells by these anti-tumor effectors, apoptosis is brought about in the tumor cells;

3) The type I interferon activates NK cells that selectively damage virus-infected cells, and induces NK cell-induced apoptosis in the tumor cells.

Further, as described above, the type I interferon participates inhibition of T cell activation, and enhancement of T cell suppressor activity. Therefore, it is considered that some kinds of autoimmune diseases can be ameliorated by the type I interferon.

Because of the anti-virus effect and anti-tumor effect as mentioned above of the type I interferon, interferon α formulation and interferon β formulation have been used for treating hepatitis B, hepatitis C, hepatitis C-induced liver and kidney cancers, and the like. For example, "Sumiferon (Registered Trademark)" made by Sumitomo Pharmaceuticals, which is a wild type interferon α, are used successfully in clinical applications.

However, the researches on TLR that have been carried out so far indicate that the signaling pathway leading to the type I interferon production induced by TLR3 witch recognized double-stranded RNA is different from the signaling pathways mediated via other TLRs. However, it has not been understood which protein participates in the signaling pathway.

It is believed that discovery of existence of a protein that induces the signaling by specifically binding to TLR3, the signaling causing the type I interferon production in downstream will lead to understanding of a signaling pathway important for innate immune response against viruses and a control mechanism of the signaling pathway. The understanding of the signaling pathway and its control mechanism is expected to be used in pathological analysis of various illnesses relating to the innate immune system and development of therapeutic agents that control innate immune response.

Moreover, the interferon formulations used for viral infectious diseases and tumors is for systemic administration: at therapeutic concentrations the interferon formulations have strong side effects such as worsening pschoneurosis (depression and the like), autoimmune disease (thyroid insufficiency, autoimmune hepatitis, hemolytic anemia, ulcerative colitis, rheumatoid arthritis, and the like), and the like side effect. The side effects caused by the interferon formulations occur presumably because interferon is introduced even in normal host cells that do not produce interferon, thereby inducing presentation of autoantigen to T cells in all portions where the interferon is induced, and thus making it easy to cause autoimmune phenomenon to occur, even though the presentation of antoantigen to T cells is normally caused when immune responds to exogenous antigen.

Because they have strong side effects at their therapeutic concentration, the interferon formulations have difficulties to maintain sufficient anti-cancer effect if systemically administered. Moreover, even if administered locally, it is considered that the side effects are difficult to avoid completely. It is considered that if a novel protein that specifically binds to TLR3 so as to induce the downstream signaling that leads to the type I interferon production is found out, it will be possible to develop a new therapeutic agent for treating a viral infectious disease, tumor, or the like by locally enhancing the type I interferon production in vivo.

Moreover, functional analysis of the novel protein is expected to provide a protein that inhibits the type I interferon production in vivo. Further it will be possible to provide a therapeutic agent that inhibits the type I interferon production in vivo by this protein thereby treating autoimmune disease, atopic disease, and the like.

In view of the foregoing problems, an object of the present invention is to provide a novel adaptor protein and its mutants, a gene of the protein, a recombinant expression vector including the gene, an antigen against the protein, and a therapeutic agent for preventing or treating a viral infectious disease, a therapeutic agent for treating a tumor, a therapeutic agent for treating autoimmune disease, and atopic disease.

DISCLOSURE OF THE INVENTION

In order to attain the object, the inventors of the present invention accomplished the present invention.

The inventors of the present invention recently found out that human TLR3 transmits a signal to indicate presence of double-stranded RNA (ribonucleic acid) independent of the currently known adaptor molecules MyD88 and Mal/TIRAP, thereby to induce interferon (IFN) β production, the adaptor molecule MyD88 considered to be essential to all signalings of the TLR family known at present, and the adaptor Mal/TIRAP being able to associate with TLR4. As a result of diligent works on novel adaptor protein having a property of specifically binding to mammalian Toll-like receptor 3, the inventors of the present invention identified a novel adaptor protein having the property of specifically binding to mammalian Toll-like receptor 3, and determined a full-length gene sequence of the novel adaptor protein. Further, the inventors of the present invention found out that the novel protein has a function of activating a nuclear factor and inducing interferon β production.

A protein according to the present invention is a protein having an amino acid sequence set forth in SEQ ID NO: 2 or 4, or mutants thereof.

As described later, the inventors of the present invention firstly identified this novel protein and determined its full-length amino acid sequences. This novel protein is named "TICAM-1" (hereinafter, this protein is referred to as "adaptor protein TICAM-1" where appropriate). SEQ ID NO: 2 illustrates an amino acid sequences derived from human, while SEQ ID NO: 4 illustrates an amino acid sequence derived from mouse. The adaptor protein TICAM-1 was, as described above, confirmed to bind to TLR3 specifically but not other TLRs, TLR3 mutants, and the like, and to having a function of activating mammalian nuclear factor κB (NF-κB) and interferon β promoter, thereby inducing interferon β production.

Therefore, the protein can enhance mammalian type I interferon production. Thus, by using the anti-virus effect and anti-tumor effect of the type I interferon it is possible to prevent/treat (prevent or treat) viral infectious diseases such as hepatitis B, hepatitis C, and the like, to perform autoimmune therapy or the like for tumor (cancer).

It has been proved that viral double-stranded RNA plays a role in most of viral infectious diseases. Recognition of this double-stranded RNA by TLR3 induces the type I interferon production via TICAM-1 mediated signaling pathway. Therefore, administration of the adaptor protein TICAM-1 to a viral infectious disease reinforces immune response of innate immune system against the viral infectious disease.

Therefore, it is possible to prevent or treat the virus infectious disease by the anti-virus effect of type I interferon, while avoiding side effects such as autoimmune diseases caused by introduction of type I interferon in body part that is not infected with virus.

Moreover, as described later, it was confirmed that the adaptor protein TICAM-1 solely induces the type I interferon production, without associating with TLR3. Thus, the adaptor protein TICAM-1 can induce the type I interferon production even without viral infection, and is effective for various diseases that can be ameliorated by the interferon I production. For example, the administration of the adaptor protein TICAM-1 to tumor can induce the type I interferon production. Therefore, the use of type I interferon can treat the tumor.

Moreover, the protein proves that there is a new TLR3-mediated signaling pathway that is independent of the adaptor molecule MyD88 and Mal/TIRAP. This new signaling pathway explains a missing link of the signaling from TLR family to the activation of interferon β promoter activation via a TLR family. Thus, the protein is not only useful as a research material to study and analyze the TLR3-mediated signaling and control mechanism, but also useful to perform, via such studies, pathological analysis on various diseases with which the signaling system and its control mechanism relate to.

It has not studied whether the protein has a function of inducing the interferon α production. However, a previous research confirmed that the interferon α production and interferon β production shares the same signaling pathway. Thus, it is presumed that the protein also has a function of inducing the interferon a production.

Here, the "protein" may be isolated and purified from cells, tissues, or the like, or may be expressed in the cells by introducing, into host cells, a gene encoding the protein. Moreover, the protein according to the present invention may contain a polypeptide additionally. An example of such polypeptide addition is epitope tagging of the protein according to the present invention with HA, Flag, or the like.

The mutants of the protein according to the present invention having the amino acid sequence set forth in SEQ ID NO: 2 or 4 have amino acid sequence set forth in SEQ ID NO: 2 or 4 in which one or more amino acids are replaced, deleted, inserted, and/or added, and either of the following features: (a) having an amino acid sequence ranging from 394-position to 532-position (TIR domain) in the amino acid sequence as set forth in SEQ ID NO: 2; (b) having an amino acid sequence ranging from 396-position to 534-position (TIR domain) in the amino acid sequence set forth in SEQ ID NO: 4; (c) a property of specifically binding to mammalian Toll-like receptor 3, and a property of inducing mammalian type I interferon; (d) the property of inducing mammalian type I interferon, and abnormality (reduction or deletion) in the property of specifically binding to mammalian Toll-like receptor 3, and (e) the property of specifically binding to mammalian Toll-like receptor 3, and abnormality in the property of inducing mammalian type I interferon. A specific example of the protein that has the feature (e) is a human protein that has the amino acid sequence set forth in SEQ ID NO: 2 in which at least amino acid 434 is replaced or deleted, and at least part of an amino acid sequence ranging from 394-position to 532-position (TIR domain) is contained.

The mutants of the proteins are not only useful as research material to study and analyze TLR3-mediated signaling system and its control mechanism, but also useful to perform, via such studies, pathological analysis on various diseases with which the signaling system and its control system involve.

Further, the mutant proteins respectively having the features (a) to (c) can enhance the mammalian type I interferon production, like the protein having the amino acid sequence set forth in SEQ ID NO: 2 or 4. Therefore, it is possible to use the anti-virus effect or the anti-tumor effect of the type I interferon, thereby to perform prevention/treatment (prevention or treatment) of the viral infectious diseases such as hepatitis B, hepatitis C, and the like, autoimmune therapy for tumor (cancer), or the like.

The mutant protein having the feature (d) can enhance the mammalian type I interferon production. Therefore, it can be used as a therapeutic agent for preventing or treating diseases (cancer or viral infectious diseases, and the like) that can be ameliorated by enhancement of type I interferon production.

The mutant protein having the feature (e) binds to TLR3 thereby to inhibit the TLR 3-mediated signaling that induces the type I interferon production. Thus, this mutant protein inhibits the type I interferon production. Therefore, it is considered that this mutant protein can be used to prevent or treat autoimmune diseases, atopic disease, and the like that are caused by the type I interferon production.

Moreover, the mutant proteins having the features (a) to (e) are useful to analyze a function of a protein, e.g., by finding which region of a protein is essential for an activity, by comparing the mutant and a wild-type protein.

The wording "one or more amino acids are replaced, deleted, inserted, and/or added" is to mean that one or more amino acids are replaced, deleted, inserted, and/or added in a number that can be replaced, deleted, inserted, and/or added by a known mutation preparation method, such as site-directed mutagenesis or the like. In other words, a protein having an amino acid sequence set forth in SEQ ID NO: 2 or 4, in which one or more amino acids are replaced, deleted, inserted, and/or added, is a mutant (mutant protein) mutated from a protein having an amino acid sequence set forth in SEQ ID NO: 2 or 4. Here, artificial mutation by a known mutation protein preparation method is mainly meant by the word "mutation". However, the mutant may be prepared by isolation and purification of such a mutant protein naturally exists.

A gene according to the present invention is a gene encoding any one of the proteins mentioned above.

The gene is useful as a research material to study and analyze the TLR3-mediated signaling system and its control mechanism. In addition, there is a possibility that, via such studies, the gene can be useful to analyze various diseases to which the signaling system and its control mechanism relate.

The "gene" encompasses at least genome DNAs, cDNAs, and mRNAs. Examples of the gene according to the present invention includes: (1) cDNA derived from human, the cDNA having, as an open reading frame, 63 to 2198 bases of base sequence shown in SEQ ID NO: 1, (2) cDNA derived from mouse, the cDNA having, as an open reading frame, 66 to 2261 bases of base sequence shown in SEQ ID NO: 3, and (3) mRNAs having base sequences corresponding to these cDNAs.

Moreover, the "gene" encompasses not only double-stranded DNAs, but also each single-stranded DNA such as sense strand and antisense strand, and RNAs. Further, the "gene" may contain another sequence than the open reading frame. The other sequence may be a sequence of an untranslated region (UTR), a vector sequence (encompassing an expression vector sequence), and other sequences. For example, the gene of the present invention may be multiplied arbitrarily by multiplying, by using an appropriate host, a gene of the present invention constituted by linking a sequence encoding the protein, to a vector sequence. Moreover, part of the sequence of the gene of the present invention may be used as a probe. Examples of cases where the gene of the present invention is used as a probe include a case where part of the sequence of the gene of the present invention is fixed on a chip thereby constituting a DNA chip and this DNA chip is used for various tests and diagnosis.

A recombinant expression vector according to the present invention contains the gene.

Use of this recombinant expression vector allows introduction of the gene in target cells by transformation of the target cells by a known genetic engineering technique (gene manipulation).

The transformant prepared by the transformation is useful as a research material to study and analyze the TLR3-mediated signaling system and its control mechanism. In addition, there is a possibility that, via such studies, the transformant can be useful to analyze various diseases to which the signaling system and its control mechanism relate.

By introducing the gene contained in the recombinant expression vector into mammalian target cells (host cells) by the transformation and expressing the gene in the target cells, it is possible to control mammalian type I interferon production. Thus, the recombinant expression vector allows gene therapy for diseases (viral infectious diseases, tumors, and the other diseases) that can be ameliorated by enhancing type I interferon production, or diseases that are caused by the type I interferon production.

An antibody according to the present invention is an antibody that specifically binds to any of the proteins mentioned above.

The antibody is expected to be useful for detection of expression of the adaptor protein TICAM-1 in host cells and production, purification, and the like, of the adaptor protein TICAM-1.

Moreover, the antibody, the antibody that specifically binds to a protein having a property of specifically binding to mammalian Toll-like receptor 3 can inhibit the type I interferon production that is caused by immune response mediated by the mammalian Toll-like receptor 3. The antibody is useful as a therapeutic agent for preventing/treating diseases (viral infectious diseases, tumors, and the other diseases) that can be ameliorated by enhancing type I interferon production.

For a fuller understanding of the nature and advantages of the invention, reference should be made to the ensuing detailed description taken in conjunction with the accompanying drawings.

BRIEF DESCRIPTION OF DRAWINGS

FIG. 5 is a view illustrating homology search for human TICAM-1 (SEQ ID NO: 2) and mouse TICAM-1 (SEQ ID NO: 4).

FIG. 6 is a view illustrating TIR domains of human TICAM-1 (SEQ ID NO: 2 from residue 394 to residue 532), mouse TICAM-1 (SEQ ID NO: 4 from residue 396 to residue 534), and known adaptor molecules Mal (SEQ ID NO: 11) and MyD88 (SEQ ID NO: 12).

FIG. 12(a) is a view illustrating measurement results of interferon β promoter activation caused by human TICAM-1 and its mutant. FIG. 12(b) is a view illustrating NF-κB activation caused by human TICAM-1 and its mutant.

BEST MODE FOR CARRYING OUT THE INVENTION

Figure 1:
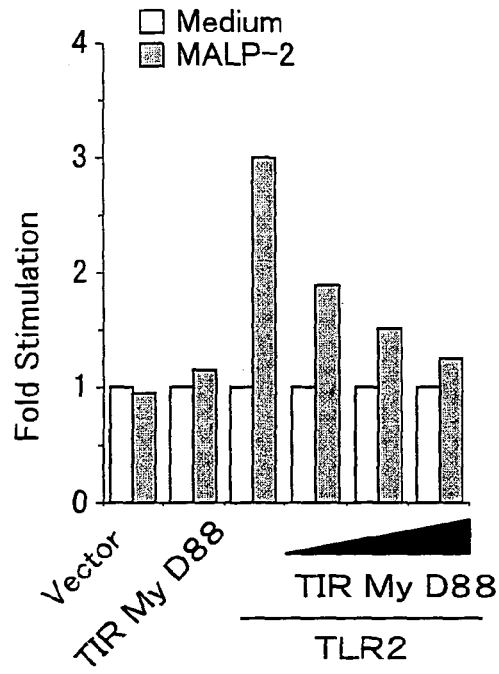
FIGS. 1(a) to 1(d) are views illustrating results of reporter gene expression assays on NF-κB activation caused by human TLR.
Figure 1:
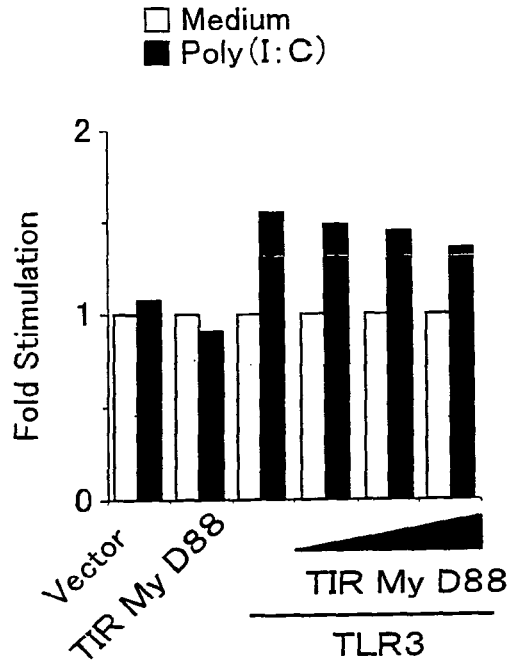
Figure 1:
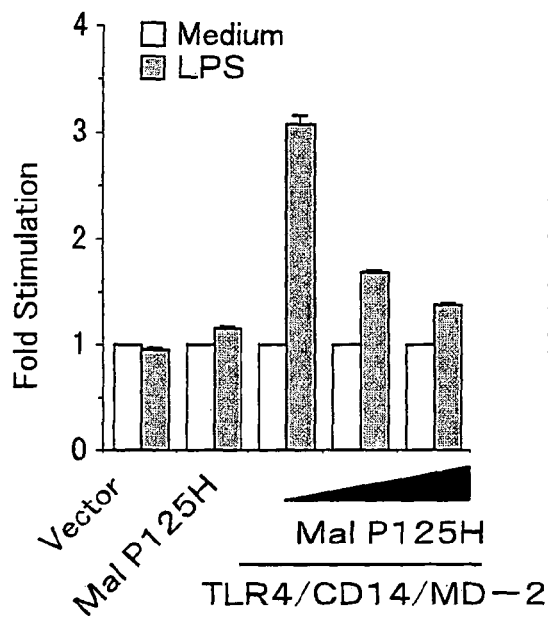
Figure 1:
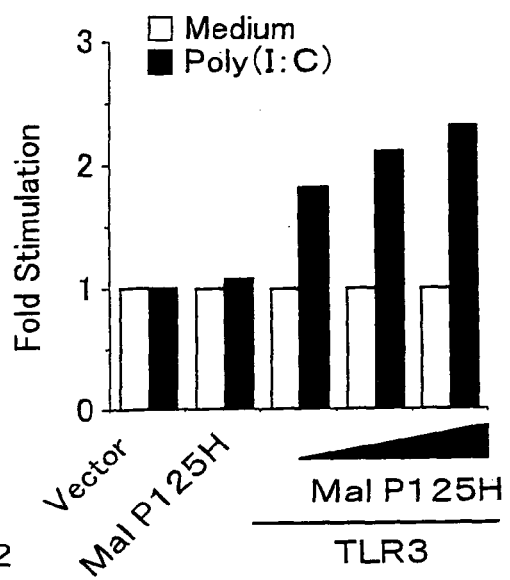

An exemplary embodiment of the present invention is described below. The embodiment is not to limit the present invention.

(1) Adaptor Protein TICAM-1 According to the Present Invention, and its Gene Sequence, Gene Structure, and the Like.

The inventors of the present invention found via experiments on transfection of HEK 293 cells described in [Examples] that TLR3 signaling induced by double-stranded RNA and mediated by human TLR3 is introduced through its cytoplasmic tail TIR, and largely independent of adaptor molecule MyD88 and Mal/TRRAP.

Based on this the inventors expected that there is another adaptor molecule that predominantly participates at least in the type I interferon promoter activation that is mediated by TLR3.

The inventors expected that there is another adaptor molecule, which preferentially mediates signaling that induces the type I interferon, but which is distinct from the already known adaptor molecule MyD88 and Mal/TIRAP. Identification of the unknown adaptor molecule was attempted.

As a result, the inventors successfully identified an alternative adaptor molecule. Physically, this alternative adaptor molecule binds to Toll/interleukin-1 receptor homology domain (hereinafter "TIR domain") of human TLR3. Functionally, the alternative adaptor molecule induces the activation of the type I interferon promoter in response to polyinosinic acid-cytidylic acid (hereinafter referred to as "poly(I:C)"). This adaptor molecule is named as "TIR domain-containing adaptor molecule" (hereinafter referred to as "TICAM-1" for abbreviation) by the inventors because it has the TIR domain.

SEQ ID NOS: 2 and 4 illustrate amino acid sequences of the adaptor protein TICAM-1 according to the present invention. SEQ ID NO: 2 illustrates an amino acid sequence of an adaptor protein TICAM-1 derived from human (abbreviated to as "human TICAM-1"). SEQ ID NO: 4 illustrates an amino acid sequence of an adaptor protein TICAM-1 derived from mouse (abbreviated as "mouse TICAM-1").

Moreover, SEQ ID NOS: 1 and 3 illustrate base sequences of full-length cDNA sequence encoding the adaptor proteins TICAM-1. SEQ ID NO: 1 illustrates full-length cDNA sequence encoding the human TICAM-1, while SEQ ID NO: 3 illustrates full-length cDNA sequence encoding the mouse TICAM-1.

In the base sequence of SEQ ID NO: 1, positions 63 to 2198 in the base sequence corresponds to open reading frame (ORF) encoding the human TICAM-1. In the base sequence of SEQ ID NO: 3, positions 66 to 2261 in the base sequence correspond to open reading frame (ORF) encoding the mouse TICAM-1. Each of the cDNA sequences of SEQ ID NOS: 1 and 3 contains untranslated regions (UTR) on 5' and 3' ends.

It was found that the human TICAM-1 is made of an N-terminal proline-rich domain (from 1-position to 393-position in the amino acid sequence), TIR domain (from 394-position to 532-position in the amino acid sequence), and, a C-terminal proline-rich domain (from 532-position to 712-position in the amino acid sequence) (FIG. 5).

The TIR domain of the cDNA sequence of human TICAM-1 has low similarity to TIR domains of the known adaptor molecules, human Mal/TIRAP (c.f. Non-Patent Documents 3 and 4) (i.e., "Mal (TIR).hu" and "MyhD88 (TIR).hu of FIG. 6) and human MyD88. Further, the TIR domain of the cDNA sequence of human TICAM-1 is unique in that (F/Y)D in Box1, RD in Box 2, and FW in Box 3 (c.f. Xu et al., Structural basis for signal transduction by the Toll/interleukin-1 receptor domains, Nature 408: 111-115, 2000), which are conserved sequences in the TIR domains of other TIR domain containing proteins, are missing in the TIR domain of the cDNA sequence of human TICAM.

In contrast, in the human TICAM-1, the prolines in so-called BB loop (c.f. Xu et al., Structural basis for signal transduction by the Toll/interleukin-1 receptor domains, Nature 408: 111-115, 2000) were well conserved. The prolines in BB loop are essential for the signaling via TIR-MyD88 and conserved in the known adaptor molecule MyD88 and Mal/TIRAP.

Another important difference between (i) the human TICAM-1 and (ii) the known adaptor molecule MyD88 and Mal/TIRAP is in that a Death domain (cell death inducing region) or an shorter Mal-like N-terminal domain is deleted in the human TICAM-1, and the human TICAM-1 contains a proline-rich long N- and C-terminal stretches:

Moreover, a database search through human genome draft sequence using the cDNA sequence of the human TICAM-1. The database search showed that the cDNA sequence encoding the human TICAM-1 is located in chromosome 19p13.3 (gene situ).

The proteins and genes are likely applicable for use in diagnosis. It is expected that, by detecting whether or not the adaptor protein TICAM-1 or a mutant similar thereto in function is expressed in cells sampled from an individual to be diagnosed, it is possible to diagnose the individual has an immunodeficiency syndrome that is caused by depletion or mutation in the adaptor protein TICAM-1. As methods to detect the expression of the adaptor protein TICAM-1 or the mutant similar thereto in function the following methods are considered as applicable: to detect the gene of the adaptor protein TICAM-1 by using DNA-tip; to test single nucleotide polymorphisms (SNPs) of a gene of the adaptor protein of the individual; and the other methods.

(2) Preparation Method of Proteins and Genes According to the Present Invention

Here, how to obtain the proteins and genes according to the present invention is explained.

There is no particular limitation as to how to obtain the gene encoding the adaptor protein TICAM-1. By using various methods, the gene encoding the adaptor protein TICAM-1 may be cloned from a DNA fragment containing the gene sequence, based on the disclosed sequence information mentioned above. For example, a probe may be prepared which specifically hybridizes with part of the sequence of cDNA encoding the adaptor protein TICAM-1, so that screening may be performed through human or mouse genomic DNA library or cDNA library with the probe.

The probe may have any sequence and length, as long as it specifically hybridizes with at least part of (i) the base sequence of the cDNA encoding the adaptor protein TICAM-1 or (ii) its complementary sequence.

A clone thus obtained through the screening can be analyzed in more detail by constructing a restriction map and determination of its base sequence (sequencing). These analysis methods make it possible to easily check whether a DNA fragment including the gene sequence according to the present invention is obtained or not.

Moreover, by selecting a sequence of the probe from among TIR domains considered to be important in the functions of the adaptor protein TICAM-1, and screening through human, mouse, or other mammal's cDNA library, it is possible to isolate a gene encoding a homologous molecule or analogue molecule having a function similar to that of the adaptor protein TICAM-1, and perform cloning with the gene.

The gene (polynucleotide) according to the present invention can be obtained by amplification means such as PCR or the like, apart from the screening methods. For example, it is possible to mass-produce a DNA fragment including the polynucleotide according to the present invention by preparing primers respectively from the sequence (or complementary sequence thereof) of the untranslated regions at 5' and 3' ends among the cDNA sequences of the adaptor protein TICAM-1, and then performing PCR or the like using the primer and a human/mouse genome DNA (or cDNA) or the like as a template. There is no particular limitation in how to obtain the protein according to the present invention. For example, the gene thus obtained (i) the cDNA encoding the adaptor protein TICAM-1, (ii) the cDNA encoding the homologous molecule thereof or the like, (iii) or the like) may be introduced in a microorganism (such as *Escherichia coli*, yeast, or the like), animal cells, or the like, so as to perform expression and purification of the protein encoded by the cDNA. This allows easy preparation of the protein according to the present invention, such as the protein adaptor protein TICAM-1, and the like.

In case of introducing the extraneous gene in the host, there are various recombinant expression vector and hosts available. Into their extraneous gene recombination region of the recombinant expression vector a promoter that can function in the host is inserted. It is possible to select the recombinant expression vector and the host according to purposes. Depending on the host used and property of the protein thus produced, a different method is applied to collect the protein after the production. It is possible to purify the targeted protein relatively easily by using a tag or the like.

(3) Adaptor Protein TICAM-1 and Usefulness of its Gene and the Like

The adaptor protein TICAM-1 can accelerate the type I interferon production by the following function mechanisms.

(a) In a host cell which is infected with a virus and in which TLR3 is expressed, the adaptor protein TICAM-1 binds to TLR3 that recognized the double-stranded RNA from the virus. The binding induces signaling that leads to induction of downstream type I interferon production. The signaling strongly enhance the type I interferon production. Thereby, the type I interferon production can be strongly enhanced cell-specifically (locally) in the host cell infected with the virus. That is, it is possible to enhance the immune response against viruses.

(b) In a host cell which is not infected with the virus, the adaptor protein TICAM-1 is solely expressed, thereby to induce the signaling that induces the downstream type I interferon production. This enhances the type I interferon production. The sole expression of the adaptor protein TICAM-1 also has a high type I interferon induction activity. However, an amount of the type I interferon is smaller in this function mechanisms (b) than in the function mechanisms (a).

As a result, the adaptor protein TICAM-1 is useful as follows.

1) The adaptor protein TICAM-1 or a mixture containing the adaptor protein TICAM-1 as an active ingredient is quite useful as a therapeutic agent for preventing/treating a viral infectious disease. That is, mainly as a result of the enhancement of the type I interferon production by the function mechanisms (a), it is possible to enhance the type I interferon-caused anti-virus effect specifically (locally) in the virus-infected host cell. That is, it is possible to allow type I interferon to have a greater bio-defense function against the virus infection. Therefore, it is possible to prevent or treat the virus infectious disease while keeping, as low as possible, the side effect (such as autoimmune disease and the like) due to excess production of type I interferon. Examples of the virus infectious disease to which the present invention is applicable include any illness that has been confirmed that the type I interferon is effective, that is, viral hepatitis B and hepatitis C (especially of genotype IIa) and the like. Moreover, the present invention is expected to be applicable to Acquired Immune Deficiency Syndrome (AIDS; immunologic unresponsiveness-causing infection disease) caused by human immunodeficiency virus (HIV). Moreover, the adaptor protein TICAM-1 can prevent virus infection by expressing the adaptor protein TICAM-1 at a portion at which latent infection is suspected. Moreover, the adaptor protein TICAM-1 exhibits a high type I interferon induction activity even if solely expressed (i.e., in the function mechanisms (b)). Thus, the adaptor protein TICAM-1 exhibits a sufficient anti-virus effect even without TLR3 expression (i.e., in case where the function mechanism (a) is not effective).

2) The adaptor protein TICAM-I or the mixture containing the adaptor protein TICAM-1 as the active ingredient is useful as the therapeutic agent for tumor treatment. That is, the enhancement of the type I interferon by the function mechanisms (b) results in enhancement of the anti-tumor effect by the type I interferon. This makes it possible to treat tumor (cancer) by innate immunity therapy. Examples of the tumor to which the present invention is applicable include malignant tumors (hepatoma, kidney cancer, juvenile pharynx/villous tumor, malignant lymphoma, cerebral tumor, glioblastoma, medulloblastoma, astrocytoma, dermal malignant melanoma, and the like) that has been confirmed that the type I interferon is effective.

It is preferable that cells targeted by the therapeutic agent according to the present invention be cells that express, on theirs surfaces, TLR3 that recognizes the double-stranded RNA of the virus. However, because the protein according to the present invention can solely induce the type I interferon production, the present invention is also applicable to cells that do not express TLR3 on their surfaces. However, in case where the present invention is applied to the viral infectious diseases, it is preferable that the adaptor protein according to the present invention be introduced in the cells that express, on theirs surfaces, TLR3 that recognizes the double-stranded RNA of the virus. This makes it possible to cause the type I interferon production locally in the virus-infected portion. Thus, it is possible to effectively treat the viral infectious disease by increasing the amount of the type I interferon produced, while keeping, as low as possible, the side effect caused by increasing the amount of the type I interferon.

According to the studies by the inventors of the present invention, human TLR3 is expressed in various dendritic cell (DC) subsets. Further, it has been reported that human TLR3 is expressed in human intestinal epithelial cells and human fibroblasts. (c.f. Muzio et al., J. Immunol. 164: 5998-6004, 2000; and Cario & Podolsky, Infect. Immun. 68: 7010-7017, 2000) These suggest that its function closely relates to responses of the innate immune system to a microbial nuclear constituent. Therefore, the therapeutic agent according to the present invention for treating the virus infectious disease is effective for the cells that produce the type I interferon by expressing human TLR3, especially, for the cells that produce the type I interferon when they expressing human TLR3 on their surface and recognize an RNA virus. Examples of such cells include (i) human fibroblasts such as human lung fibroblasts, human preputial fibroblasts, and the like, (ii) the human dendritic cells, (iii) human intestinal epithelial cells, (iv) and the like. Especially, the fibroblasts are known to produce the type I interferon via different signaling pathways when infected with RNA viruses or treated with the double-stranded RNA. The present invention is expected to quite effective for the fibroblasts. Moreover, examples of the cells that produce the type I interferon by expressing mouse TLR3 include mouse fibroblasts and the like.

Moreover, to administer the preventive/therapeutic agent containing the adaptor protein TICAM-1, phleboclysis, hypodermic injection, and the like injection are preferable. However, the therapeutic agent may be administered by non-oral manners such as sublingual tablet, rectal administration, and the like. Further, it is possible to prepare this therapeutic agent according to a general method of producing protein formulations. Furthermore, it is possible to use this therapeutic agent as an emulsifier for liposome formulations and the like.

The adaptor protein TICAM-1 is expected to have the following usefulness beside the one mentioned above.

As a result of the enhancement of the type I interferon production by the function mechanisms (b), the type I interferon's immune control effect is enhanced, thereby to enable a kind of autoimmune-disease treatment.

Moreover, the adaptor protein TICAM-1 is expected to be used for screening and the like of compounds that enhance the binding of TLR3 and the adaptor protein TICAM-1 or the downstream signaling from the adaptor protein TICAM-I to the type I interferon production, and compounds that inhibit (are inhibitors of) the downstream signaling from the adapter protein TCAM-1 to the type I interferon production.

Moreover, as described later in Examples, the adaptor protein TICAM-I is a molecule that binds to TLR3 and induces the type I interferon production. Thus, the adaptor protein TICAM-1 is considered to be a molecule that plays a quite important role in the signaling system through TLR3. Thus, the gene and protein according to the present invention is useful as a research material for analysis of the TLR3-mediated signaling system and its control mechanism. Through the research, the gene and protein according to the present invention may be possibly useful for pharmacologically analyzing various illnesses to which the signaling system and its control mechanism relate.

(4) Mutants of Adaptor Protein TICAM-1

There known a large number of protein mutants having similar activity and functions to their wild types. Therefore, there is no particular limitation as to how to produce a mutant of the adaptor protein TICAM-1, the mutant having both of the property of specifically binding to TLR3 and the property of inducing the type I interferon production, like the adaptor protein TICAM-1. For example, it is possible to produce the mutant by using known mutation protein preparation methods, such as a site-directed mutagenesis inducing method (Hashimoto-Gotoh, Gene 152: 271-275, 1995; and others), a method of preparing the mutant by introducing point mutation in a base sequence by using PCR or the like, a mutated strain preparation method by insertion of transposon. Moreover, the mutant may be prepared by using commercially-available mutation inducing kit (e.g., a position specific mutation inducing kit "Quick Change" by Stratagene). In this case, by inducing mutation in a position other than the TIR domain that is considered as a region that have the property of specifically binding to TLR3 and the property of inducing the type I interferon production, it is possible to surely prepare the mutant of the adaptor protein TICAM-1, the mutant having the property of specifically binding to TLR3 and the property of inducing the type I interferon production.

That is, as described later in Examples, a mutant protein had the property of specifically binding to TLR3 and the property of inducing the type I interferon production, the mutant protein made of almost only a region (TIR domain) that is homologous with the Toll/interleukin 1 receptor among the amino acid sequence constituting human TICAM-1, that is made of an amino acid sequence ranging from 387-position to 556-position. Because of this, it is expected that as long as a mutant has the TIR domain (an amino acid sequence ranging 394-position to 532-position in the amino acid sequence constituting human TICAM-1, or an amino acid sequence ranging from 396-position to 534-position in the amino acid sequence constituting the mouse TICAM-1), the mutant has the property of specifically binding to TLR3 and the property of inducing the type I interferon production.

The mutant of the adaptor protein TICAM-1 having the property of specifically binding to TLR3 and the property of inducing the type I interferon production, is similarly useful as the adaptor protein TICAM-1. That is, the mutant has usefulness as the virus infectious diseases, usefulness as a therapeutic agent for treating tumors, and other usefulness.

On the other hand, it is expected that it is possible to prepare a mutant protein having abnormality either in the property of specifically binding to TLR3 and the property of inducing the type I interferon production, by causing mutation in the TIR domain of the adaptor protein TICAM-1, the TIR domain considered as the important region for the property of specifically binding to TLR3 and the property of inducing the type I interferon production.

As described later in Examples, a mutant protein was prepared by introducing a point mutation to the mutant made of almost only the TIR domain (from 387-position to 556-position in the amino acid sequence) in the amino acid sequence constituting human TICAM-1, the point mutation substituting with histidine an amino acid (proline) at position 434 (in the full-length human TICAM-1). The mutant protein kept the property of specifically binding to TLR3, but lost the property of inducing the type I interferon production. This indicates that a mutant protein having the property of specifically binding to human TLR3 but abnormality in the property of inducing the type I interferon can be prepared by introducing mutation at least in that part, which includes amino acid 434 (proline) of the TIR domain of the adaptor protein TICAM-1 or of the mutant at least having the TIR domain.

The mutant protein having the property of specifically binding to human TLR3 but abnormality in the property of inducing the type I interferon can inhibit the signaling that leads to the type I interferon production downstream from TRL3. As a result, it is expected that this makes it possible to treat the autoimmune diseases, atopic diseases, and the like illness caused by the signaling pathway mediated by the control of the adaptor protein TICAM-1 and leading to the type I interferon production downstream from TLR3. Specifically speaking the mutant protein is useful as follows:

a) The mutant protein or a mixture containing it as an active ingredient is useful as a therapeutic agent for treating the autoimmune diseases.

b) The mutant protein or a mixture containing it as an active ingredient is useful as a therapeutic agent for treating the atopic diseases.

On the other hand, it is expected that a mutant protein keeping the property of specifically binding to human TLR but having abnormality in the property of inducing the type I interferon production can be prepared by introducing mutation in that part, which does not include the amino acid 434 (proline) of the TIR domain of human TICAM-1 or its mutant of at least having the TIR domain so that the property of specifically binding to human TLR3 is lost.

The mutant protein keeping the property of specifically binding to human TLR but having abnormality in the property of inducing the type I interferon production is expected to be useful as a therapeutic agent for preventing/treating the virus infectious diseases, and for treating the tumors, like the adaptor protein TICAM-1. The usefulness of the mutant protein as the therapeutic agent for preventing/treating the virus infectious diseases is, however, obtained as a result of the enhancement of the type I interferon production by the function mechanisms (b) (sole expression of the adaptor protein TICAM-1), but not the enhancement of the type I interferon production by the function mechanisms (a) (virus immune response). Therefore, the mutant is inferior to the adaptor protein TICAM-1 in terms of the inhibition of the side effect such as autoimmune diseases, and virus inhibition.

(5) Recombinant Expression Vector

A recombinant expression vector according to the present invention contains the gene encoding the adaptor protein TICAM-1 or its mutant.

The recombinant expression vector is useful as a research material to analyze the TLR3-mediated signaling and its control mechanism by introducing the recombinant expression vector into various cells and expressing the adapter protein TCAM-1 in the cells. The recombinant expression vector is not only useful as a research material for analysis of the TLR3-mediated signaling and its control mechanism. Through the research, the gene and protein according to the present invention may be possibly useful for pharmacologically analyzing various illnesses to which the signaling and its control mechanism relate.

Moreover, it is possible to attain in vivo production of the adaptor protein TICAM-1 or its mutant by introducing the gene contained in the recombinant expression vector into a known mammalian target cell (host cell) using a gene transfer method and express the gene in the cell. Therefore, the recombinant expression vector is useful like the protein that is coded by the gene that the recombinant expression vector contains. That is, the recombinant expression vector is (i) useful as a therapeutic agent for preventing/treating the virus infection, (ii) useful as a therapeutic agent for treating tumor, (iii) useful as a therapeutic agent for treating the autoimmune diseases, and (iv) useful as a therapeutic agent for treating the atopic diseases. There is no particular limitation as to how to introduce the gene into the mammalian target cells, by using the recombinant expression vector. For example, the gene may be introduced by: (1) a method including sampling the target cell from an disease portion of a mammal, introducing the recombinant expression vector into the target cell thus sampled, and returning the target cell into a body of the mammal; (2) a method including introducing, locally into an organ or disease portion of the mammal, the recombinant vector together with cationic liposome;

(3) a method including introducing the gene into the target cell by using, as the recombinant expression vector, a virus vector such as retrovirus vector, adenovirus vector, and the like, by means of an infection ability of the virus vector; (4) an electroporation method including applying a constant electric field via electric electrodes after introducing the recombinant expression vector locally into an organ or disease portion of the mammal; and the other methods.

In case where the adaptor protein TICAM-1 is systemically administered to a tumor, the type I interferon production is enhanced not only in the tumor section but also in other parts of the body. Thus it is expected that it is difficult to maintain a sufficient anti-tumor effect while avoiding the side effects caused by the type I interferon. On the other hand, by locally increasing concentration of the adaptor protein TICAM-1, e.g., by the gene transfer methods mentioned above, it is possible to realize a more appropriate method for treating the tumor. Thus, the recombinant expression vector is very useful as a therapeutic agent for treating the tumor.

(6) Antibody Against Adaptor Protein TICAM-1

An antibody according to the present invention is an antibody that specifically binds to the adaptor protein TICAM-1 or its mutant.

The antibody is considered to be useful for detecting whether the adaptor protein TICAM-1 is expressed in the host cell, for producing/purifying the adaptor protein TICAM-1, and for other purposes.

Further, it is expected that the type I interferon production can be inhibited by blocking the signaling to the type I interferon production downstream from TLR3 by the antibody that specifically binds to the adaptor protein TICAM-1, or that specifically binds to the mutant of the adaptor protein TICAM-1, the mutant having the property of specifically binding to TLR3 and the property of inducing the type I interferon. Thus, it is expected that the antibody is useful as a therapeutic agent for treating the autoimmune diseases and a therapeutic agent for treating the atopic diseases, like the mutant protein having the property of specifically binding to TLR3 but having abnormality in the property of inducing the type I interferon. Moreover, it is expected that efficiency of introducing a gene of interest into the host cell by the virus vector can be improved by infecting the host cell with the virus vector in which the gene of interest is inserted while the type I interferon production is inhibited by using the antibody.

Moreover, the antibody is possibly useful as a therapeutic agent for diagnosis. That is, by detecting, by using any one of the antibodies, whether the adaptor protein TICAM-1 (or a mutant having the similar function) is expressed in a cell sampled from an individual to be diagnosed, it is expected that, based on a result of the detection, the individual can be diagnosed as to whether the individual has an immunodeficiency caused by deletion or mutation of the adaptor protein TICAM-1.

The antibody may be a monoclonal antibody or polyclonal antibody, even though it is preferable that the antibody be monoclonal, because homogenous property of the monoclonal antibody allows easy supply, it can be changed to a human antibody in the future, it can be preserved as hybridoma, and because of the other reasons.

The monoclonal antibody can be prepared by the following methods. That is, firstly, a mouse is immunized with the adaptor protein TICAM-1, its fragment, or another derivative thereof, or its analog, or a cell that expresses these, as an immunogen. Then, a hybridoma is prepared by the fusing of the immunized mouse spleen lymphocyte and a mouse myeloma cell.

Next, the monoclonal antibody is produced from the hybridoma. The immunity control can be performed according to various known methods, such as a hybridoma method (Kohler & Milstein, Nature 256: 495-497, 1975), trioma method, human B-cell hybridoma method (Kozbor, Immunology Today, 4: 72, 1983), EBV-hybridoma method (*Monoclonal Antibodies and Cancer Therapy*, Alan R Liss, Inc., pp. 77-96, 1985), and other methods.

The present invention is described below in more details referring to Examples. Note that the present invention is not limited by the description in Examples and can be modified in many ways within the scope of the present invention.

[Cell Line and Cell Cultivation]

Human lung fibroblast cell line MRC-5 was obtained from deposit at "Riken Cell Bank" of Institute of Physical and Chemical Research (3-1-1, Koyadai, Tsukuba City, Ibaraki Prefecture). Moreover, human epithelial cell line HeLa was kindly provided from Dr. Takashi FUJITA (Tokyo Metropolitan Institute of Medical Science). Further, HEK (Human Embryo Kidney) 293 cell line used in Examples did not express Human TLR3. For mRNA of human TICAM-1, HEK 293 cell line expressed an extremely low-level of mRNA of human TCAM-1 (not shown).

The cell line MRC-5 and cell line HeLa were cultured in MEM (Modified Eagle Medium). In MEM, for HeLa, an antibiotic and 5 wt % of heat-inactivated FCS (made by JRH Biosciences) had been added, while for MRC-5, the antibiotic and 10 wt % of heat-inactivated FCS had been added. The HEK 293 cells were cultured in DMEM (Duldecco's Modified Eagle Medium) to which the antibiotic and 10 wt % of heat-inactivated FCS had been added.

[Reagents]

Poly(I:C) was purchased from Amersham Pharmacia Biotech. Polymixin B, lipopolysaccharide (LPS, a cell wall constituent of gram-negative bacteria recognizable for Human TLR4, hereinafter "LPS") from *Esherichia coli* serotype 0111:B4, and mouse IgG1 were purchased from Sigma. Mycoplasma lipopeptide MALP-2 was prepared as described in Nishiguchi et al. (J. Immunol. 166: 2610-2616, 2001).

These reagents, except LPS, were treated with polymyxin B (10 µg/ml) at 37° C. for one hour before cell stimulation.

[Monoclonal Antibody Against Human TLR]

Monoclonal antibody (TLR 3.7) against human TLR3 and monoclonal antibody (TLR 2.45) against human TLR2 were produced by as described in Non-Patent Document 1 (see also Xu et al., Structural basis for signal transduction by the Toll/interleukin-1 receptor domains, Nature 408: 111-115, 2000). Monoclonal antibody against human TLR4 was kindly provided from Dr. Kensuke MIYAKE (Institute of Medical Science, the University of Tokyo) (as to preparation thereof, see Shimazu et al., J. Exp. Med. 189: 1777-1782, 1999).

[cDNA Expression Vector]

cDNAs of Human TLR2, human TLR3, MyD88, and Mal/TIRAP were generated by PCR using cDNAs obtained from human monocytes cultured for 9 days together with recombinant human GM-CSF (Made by Peprotech). Then the cDNAs were cloned into a mammalian expression vector pEFBOS, thereby producing human TLR2 expression vector, human TLR3 expression vector, MyD88 expression vector, and Mal/TIRAP expression vector. The expression vector pEFBOS was a plasmid vector kindly provided from Professor Shigekazu NAGATA at Osaka University.

The human TLR4 expression vectors and MD-2 expression vectors were kindly provided from Dr. Kensuke MIYAKE (Institute of Medical Science, the University of Tokyo).

Human TLR4 expression vector, which was flag-tagged (flag-labeled) at its N-terminal), and human TLR2 expression vector, which was flag-tagged at its N-terminal, were prepared by placing (i) cDNAs encoding human TLR4 or human TLR2 in (ii) a plasmid vector pCMV-Flag (made by Sigma) having a flag-tag at its N-terminal.

Human CD14 expression vector (pME18S/CD14) was kindly provided from Dr. Hitoshi NISHIMURA (University of Tsukuba University).

cDNA encoding a human TLR3 mutant in which TIR domain is deleted (this mutant is a protein having an amino acid sequence ranging from 1-position to 729-position in the amino acid sequence constituting TLR3; hereinafter "human TLR3deICYT") was generated from cDNA of human TLR3 by PCR (Polymerase Chain Reaction). This cDNA was cloned into the expression vector pEFBOS so as to obtain human TLR3deICYT expression vector.

cDNA encoding a dominant-negative mutant of human MyD88 (this mutant is a protein having an amino acid sequence ranging from 152-position to 296-position in the amino acid sequence constituting the adaptor protein MyD88 derived from human) was generated from cDNA of myeloid cell line P39 by PCR, and cloned into the expression vector pEFBOS, so as to obtain TIRMyD88 expression vector.

An expression vector encoding a human TLR3 mutant (Ala795His; hereinafter "human TLR3 A795H") in which amino acid 795 (alanine) was replaced with histidine, and cDNA encoding a dominant-negative mutant of adaptor molecule Mal/TIRAP (Mal Pro 125H is; hereinafter, this dominant negative mutant is referred to as "MalP125H"; MalP125H is an adaptor molecule Mal/TIRAP mutant in which amino acid 125 (proline) was replaced with histidine) were generated from human TLR 3 or Mal/TIRAP by using "Quick-change" site-directed mutagenesis kit (made by Stratagene). Then, the cDNAs encoding human TLR3 A795H and cDNA encoding MalP125H were respectively cloned into plasmid vector pEFBOS, so as to obtain human TLR3 A795H expression vector and MalP125 expression vector.

Example 1

Reporter Gene Assay

Investigated here was whether, as a result of HEK293 cell transfection, human TLR3 perform signaling mediated by the adaptor molecule MyD88 or Mal/TIRAP in response to poly (I:C) analogous to double-stranded RNA.

Firstly, reporter gene assay was performed to find level of NF-κB activation.

HEK (human embryo kidney) 293 cells ($2 \times 10^5$ cells per well) were transiently transfected in 24-well plates using gene transfecting cationic lipid "Lipofectamine 2000" reagent (made by Gibco), with a luciferase-linked NF-κB reporter gene (made by Stratagene, 0.1 µg), together with the followings: (1) empty vector, (2) TIRMyD88 expression Vector (0.2 µg), (3) TIRMyD88 expression vector (0, 0.05 µg, 0.2 µg, or 0.6 µg) and human TLR2 expression vector (0.1 µg), (4) empty vector, (5) TIRMyD88 expression vector (0.2 µg), (6) TIRMyD88 expression vector (0, 0.05 µg, 0.2 µg, or 0.6 µg) and human TLR3 expression vector (0.1 µg), (7) empty vector, (8) MalP125H expression vector (0.2 µg), (9) MalP125H expression vector (0, 0.2 µg, or 0.6 µg) and human TLR4/CD14/MD-2 expression vector (0.3 µg), (10) empty vector, (11) MalP125H expression vector (0.2 µg), (12) MalP125 expression vector (0, 0.2 µg, or 0.6 µg) and human TLR3 expression vector (0.1 µg). A total amount (0.8 µg to 1.0 µg) of transfected DNA was adjusted by adding the empty vectors. Moreover, plasmid vector pCMVβ (made by Clontech; 5 ng) was used as an internal control.

The "empty vector" was plasmid vector pEFBOS in which no cDNA was placed. Moreover, the "human TLR4/CD 14/MD-2 expression vector" was a combination of human TLR4 expression vector, human CD14 expression vector, and MD-2 expression vector.

Twenty four hours after the transfection, transfected cells were stimulated for 6 hours in the following manner: transfected cells (1) to (3) with medium alone or with MALP-2 (100 nM) treated with polymyxin B; transfected cells (4) to (6), and (10) to (12) with medium alone or with poly(I:C) (10 µg/ml) treated with polymyxin B; transfected cells (7) to (9) with medium alone, or with LPS (100 ng/ml). After that, the cells were lysed with an lysis buffer (made by Promega). Then luciferase activities of thus prepared lysates were measured following the manufacturer's instruction (the luciferase activity indicate level of NK-κB activation by the stimulation after transfection). Measurement values were representative of three independent experiments.

In FIGS. 1(a) to 1(d), the measurements values of the luciferase activities of the cells stimulated after the transfection were illustrated in gray or black, while the measurement values of the luciferase activities of the cells not stimulated after the transfection (i.e., stimulated with medium alone) are illustrated in white. The measurement values of the luciferase activities are illustrated in relative values (fold stimulation) where the measurement values of the luciferase activities not stimulated after the transfection are put as 1.

Next, reporter gene assay was performed with p-125luc reporter plasmid in order to investigate the level of interferon β promoter activation.

This "p-125luc reporter plasmid" was kindly provided from Professor Tadatsugu TANIGUCHI at Graduate School of Medical Science, the University of Tokyo (Taniguchi et al., Annu. Rev. Immunol. 19: 623-655, 2001). The p-125luc reporter plasmid was prepared by inserting a region (−125 to +19) encoding a human interferon β promoter into a reporter gene expression vector. Here, the reporter gene expression vector was "Picagene", luciferase reporter plasmid (made by Toyo Ink MFG. Co., Ltd.).

The reporter gene assay using the p-125luc reporter plasmid was performed in the similar manner to the reporter gene assay using the luciferase-linked NF-κB reporter gene, except that: in lieu of the luciferase-linked NF-κB reporter gene, p-125luc reporter plasmid (0.1 μg) was used; in lieu of the vectors (1) to (3), (1') empty vector, (2') MalP125H expression vector (0.2 μg), and (3') MalP125H expression vector (0, 0.2 μg, or 0.6 μg) and human TLR4/CD14/MD-2 expression vector (0.3 μg) was used; and the cells transfected with the vectors (1) to (3) were stimulated with medium alone or with LPS (100 ng/ml).

Then, luciferase activities were measured, which indicate level of interferon β promoter activation by the stimulation after the transfection. Measurement values obtained were given in FIGS. 2(a) to 2(d) in the same manner as FIGS. 1(a) to 1(d).

In the present Example, the following results were obtained.

Firstly, the expression of the dominant-negative mutant TIR MyD88 of the adaptor molecule MyD88 inhibited the human TLR2-mediated NF-κB activation caused by the human TLR2 ligand MALP-2 in a dose-dependent manner (FIG. 1(a)).

Figure 2:
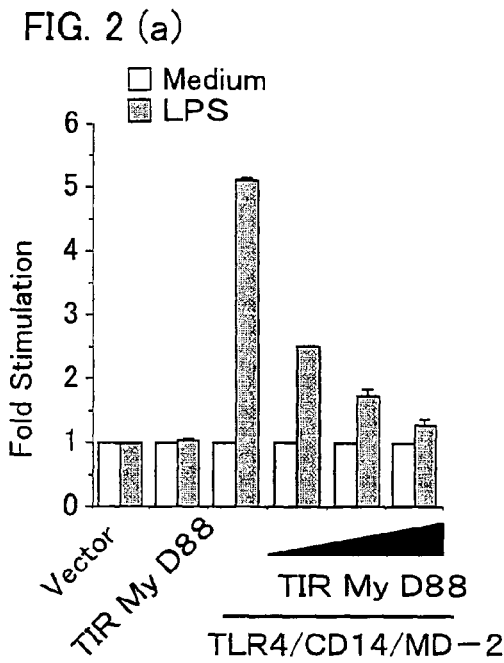
FIGS. 2(a) to 2(d) are views illustrating results of reporter gene expression assays on interferon β promoter activation caused by human TLR.
Figure 2:
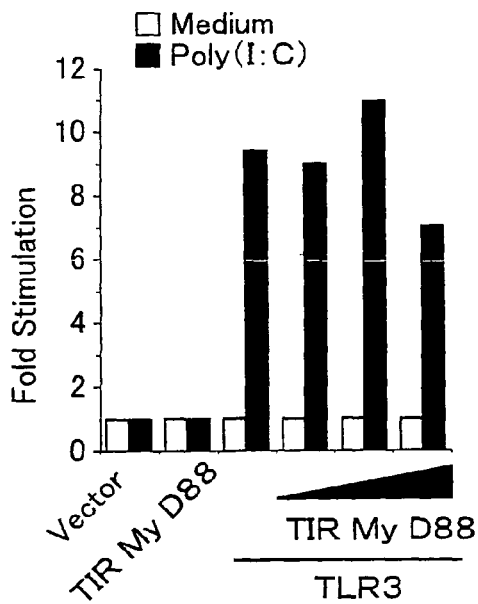
Figure 2:
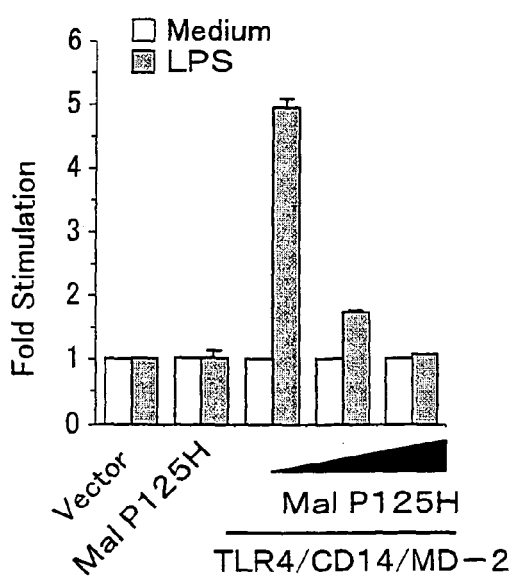
Figure 2:
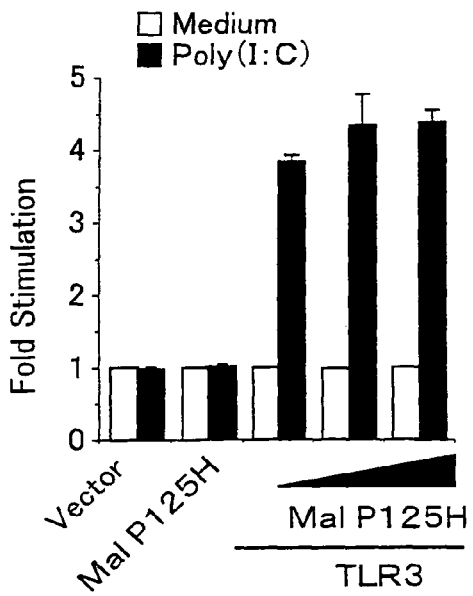

On the other hand, the expression of the dominant-negative mutant TIR MyD88 of the adaptor molecule MyD88 had very little effect on the NF-κB activation and interferon β promoter activation, which are mediated by human TLR3 and caused by poly(I:C) (c.f. FIGS. 1(b) and 2(b)).

The similar experiment using the dominant-negative mutant MalP125H of the adaptor molecule Mal/TIRAP showed that the adaptor molecule Mal/TIRAP does not contribute to the human TLR3-mediated signaling (c.f. FIGS. 1(d) and 2(d)).

In contrast, the TLR4-medicated activation of NF-κB and interferon β promoter by LPS was inhibited by the dominant-negative mutant MalP125H of the adaptor molecule Mal/TIRAP, in a dose-dependent manner (c.f. FIGS. 1(c) and 2(c)).

From the above results, it was understood that the human TLR3-mediated signaling that induces the interferon β production is independent of the known adaptor molecules MyD88 and Mal/TIRAP.

Example 2

Reporter Gene Assay

HEK (human embryo kidney) 293 cells ($2 \times 10^5$ cells per well) were transiently transfected in 24-well plates using gene transfecting cationic lipid "Lipofectamine 2000" reagent (made by Gibco), with a luciferase-linked NF-κB reporter gene (made by Stratagene, 0.1 μg), together with the followings: empty vector, human TLR3 expression vector (0.1 μg), human TLR3delCYT expression vector (0.1 μg), or human TLR3A795H expression vector (0.1 μg).

Twenty four hours after the transfection, the transfected cells (1) to (3) were stimulated for 6 hours with medium alone or with poly(I:C) treated with polymyxin B. Then, the cells were lysed with the lysis buffer (made by Promega). Luciferase activities in thus prepared lysates were measured. Measurement values were representative of three independent experiments.

The measurement values of the luciferase activities of the cells stimulated after the transfection are illustrated in black in FIGS. 3(a) and 3(b), while the measurement values of the luciferase activities of the cells not stimulated (stimulated with only medium after the transfection) are illustrated in while in FIGS. 3(a) and 3(b). The measurement values of the luciferase activities are expressed as relative values (fold stimulation) where the measurement values of the luciferase activities not stimulated after the transfection are put as 1.

The present invention gave the following results.

The cells transfected with cDNA encoding human TLR3delCYT, which was a protein prepared by deleting the TIR domain from human TLR3, did not respond to poly(I:C) similarly (c.f. FIGS. 3(a) and 3(b)).

The cell transfected with the cDNA encoding the mutant human TLR3 A795H of human TLR3 abolished responsiveness to poly(I:C) similarly to TLR3delCYT. This result indicates that point mutation at amino acid 795 (alanine) of human TLR3 is crucial for the downstream signaling down to NF-κB and for activation of the interferon promoter β.

Figure 3:
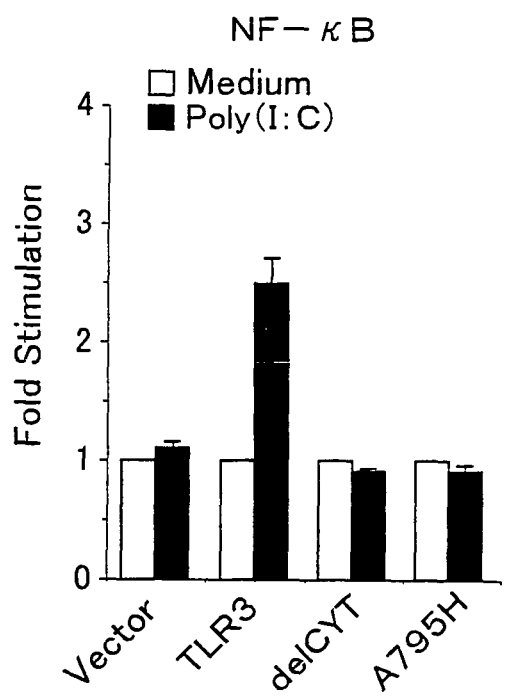
FIG. 3(a) is a view illustrating results of reporter gene expression assays on NF-κB activation caused by human TLR3 and its mutant.
FIG. 3(b) is a view illustrating results of reporter gene expression assays on interferon β promoter activation caused by human TLR3 and its mutant.
Figure 3:
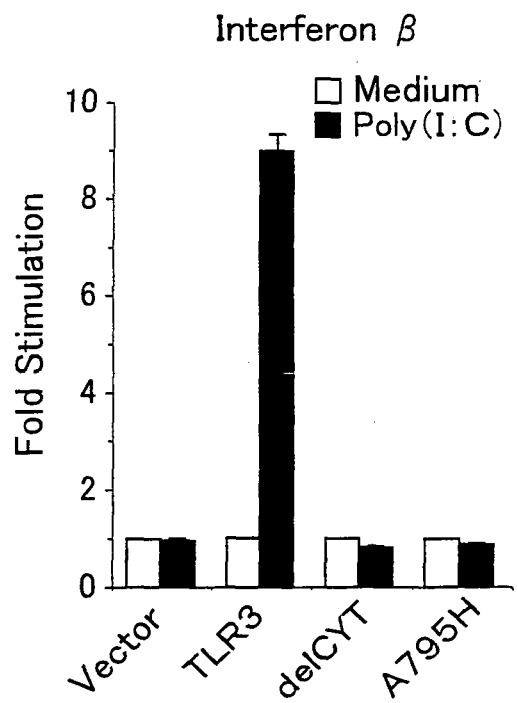

On the other hand, the cells expressing human TLR3 containing the TIR domain activated the interferon β promoter upon stimulation with poly(I:C) (see FIG. 3 (b)).

Example 3

Screening and Identification of Novel Adaptor Molecule

Figure 4:
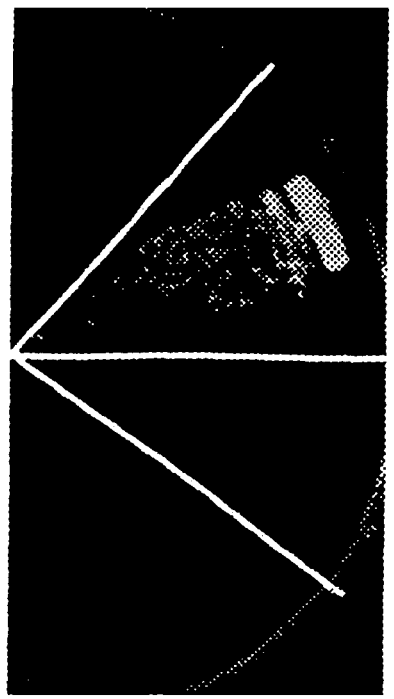
FIG. 4 is a view illustrating results of investigations on interactions between proteins by yeast two-hybrid system.

A yeast two-hybrid system showed that a tail of TLR3 was specifically associated with a certain protein (c.f. FIG. 4).

Next, to identify an adaptor molecule for human TLR 3 signaling, screening was performed by using the yeast two-hybrid system.

The screening of the novel adaptor molecule that specifically binds to TIR domain of human TLR3 was carried out by using a yeast two-hybrid system "Matchmaker two-hybrid system 3" (made by Clontech) so as to search, through a cDNA library, a protein that interacts with the TIR domain of human TLR3.

Firstly, into multicloning sites of a plasmid vector pGBKT7 (made by Clontech), which was a fusion vector of DNA binding domain of a transcription factor GAL4, cDNA encoding the TIR domain of human TLR3 and cDNA encoding the TIR domain of human TLR 4 were respectively inserted, thereby to prepare plasmid vector pGBKT7-TLR3 and plasmid vector pGBKT7-TLR4, as bait plasmid vectors. Here, the TIR domain of human TLR3 was an amino acid sequence ranging from 745-position to 904-position in the amino acid sequence constituting human TLR 3, while the TIR domain of human TLR 4 was an amino acid sequence ranging from 625-position to 799-position in the amino acid sequence constituting human TLR3.

Moreover, so-called "prey plasmid vector group" was prepared by placing "Match maker" cDNA library (made by Clontech) derived from human lung into the plasmid vector pGADT7 (made by Clontech), which was a fusion vector of activation domain of a transcription factor GAL4.

Then, a yeast strain AH109 (made by Clontech) was transformed on a yeast medium with the bait plasmid vector pGBKT7-TLR3 and the prey plasmid vector group prepared from the "Match maker" cDNA library. The yeast medium used here is described in Sherman et al., *Methods in Yeast Genetics*, Cold Spring Harbor, N.Y.: CSHL Press (1986).

In the yeast two-hybrid system, the yeast cells can grow on the plate only when the prey plasmid vector and the bait plasmid vector interact. Here, from 1,000,000 transformants to be screened, 5 clones grew on SD-Trp-Leu-His-Ade plates (SD (Synthetic Dropout) medium not containing tryptophan, leucine, histidine, and adenine).

Plasmids were recovered from the clones. Sequences of the inserted in the plasmids were analyzed.

Blast search analysis showed that clone 2.3A1-1 contained human hypothetical mRNA sequence CL24751 deduced from EST (Expressed Sequence Tag) sequence of NCBI. Twelve base pairs in 5' region of the inserts overlapped with 3' end of the hypothetical mRNA "LOC148022".

The fact that CL24751 was only 75 bp distanced from LOC148022 in human genome, and that the 3' end of LOC148022 had no terminal poly(adenyl acid) suggested that these two annotated mRNAs were derived from one transcript.

To confirm this, RT-PCR was performed using a 5' primer located in LOC148022 and a 3' primer located in CL24751. From mRNAs of various cells and tissues, the expected DNA fragment was successfully amplified. From this, the inventors of the present invention concluded that LOC148022 and CL24751 are respectively 5' fragment and 3' fragment of the cDNA for encoding the novel adaptor protein. By connecting the two cDNA fragments obtained by PCR, a full-length cDNA was obtained.

The inventors named this protein "TICAM-1 (TIR Containing Adaptor Molecule-1).

Moreover, the inventors found protein TICAM-1 (mouse TICAM-1) derived from mouse. Mouse TICAM-1 is homologous with human TICAM-1.

Firstly, a sequence homologous with human TICAM-1 was searched from the base sequence of mouse cDNA deposited in EST. As a result, mouse LOC224899 homologous with human TICAM-1 was found. This base sequence was deduced as a base sequence of cDNA encoding mouse homologue of human TICAM-1.

Screening analysis was performed by BLAST program to investigate homology between the amino acid sequence of mouse LOC224899 presumed to encode the mouse homologue of human TICAM-1 and the amino acid sequence of human TICAM-1. The result of the analysis is illustrated in FIG. 5. The amino acid sequences of the human TICAM-1 protein and the mouse TICAM-1 protein were deduced from the base sequence of cDNAs. The amino acid sequences of the proteins were aligned by using Clustal W.

In FIG. 5, "TICAM-1.hu" is the amino acid sequence of human TICAM-1, while "TICAM-1.mu" is the amino acid sequence of mouse LOC224899. In FIG. 5, asterisk (*) indicates identical residues, while double dots (:) indicates conserved substitutions, and single dot (•) indicates semi-conversed substitutions.

From the results illustrated in FIG. 5, the EST-deduced amino acid sequence of mouse LOC224899 is very similar to the amino acid sequence of human TICAM-1. This suggested that mouse LOC224899 was highly likely the mouse homologue of human TICAM-1. From this, mouse LOC224899 was identified as the mouse homologue of human TICAM-1, "mouse TICAM-1".

Moreover, human TICAM-1 and mouse TICAM-1 had TIR-like motif (TIR domain) analogous to TIR indicated by line in FIG. 5. The region was an amino acid sequence ranging from 394-position to 532-position in human TICAM-1, and an amino acid sequence ranging from 396-position to 534-position in mouse TICAM-1.

Mouse TICAM-1 was such that the proline-rich region located in N- and C-terminal domains of the TIR domain of human TICAM-1 was partially deleted (c.f. FIG. 5). Mouse TICAM-1 was 54% identical to human TICAM-1.

The cDNA sequences and amino acid sequences of human TICAM-1 and mouse TICAM-1 was deposited in DDBJ database with Genebank accession numbers AB086380 and AB091053. (They have not yet published at the filing of this application.)

Example 4

Interaction Analysis by Yeast Two-Hybrid System

Interaction between human TLR3 and human TICAM-1 was analyzed by the yeast hybrid-system.

Firstly, a plasmid vector pGADT7-TICAM-1 was prepared as so-called prey vector by placing, into multi cloning sites of the plasmid vector pGADT7 (made by Clontech), a cDNA presumed to include partial fragment of TICAM-1. Moreover, as prey vectors, a plasmid vector pGADT7 was used as a control, beside this plasmid vector pGADT7-TICAM-1.

Meanwhile, as bait vectors, the plasmid vector pGBKT7-TLR3 and pGBKTG7-TLR4, and the plasmid vector pGBKT7 (made by Clontech) were used. The plasmid vector pGBKT7 was control.

Using the same yeast medium employed in Example 4, a yeast strain AH109 (made by Clontech) was transformed with one of the two types of prey plasmid vectors (plasmid vector pGADT7 or pGADT7-TICAM-1), and one of the three types of bait plasmid vector (plasmid vector pGBKT7, pGBKT7-TLR3, or pGBKT7-TLR4), and then streak-cultured on an SD-His-Trp-Leu-Ade plate. Results are given in FIG. 4.

In this case, among all the combinations, only the combination of the prey plasmid vector pGADT7-TICAM-1 and the bait plasmid vector pGBKT7-TLR3 allowed the cell grow. Moreover, in yeast two-hybrid system using human TLR2 in lieu of human TLR3, TICAM-1 did not cloned in the yeast (not illustrated).

From this, it was confirmed that pGADT7-TICAM-1, which was identified by screening by the yeast two-hybrid system, contained partial fragment of gene encoding the adaptor protein TICAM-1 (human TICAM-1) that specifically binds to the TIR domain of human TLR3.

Example 5

Comparison of TIR Domains

Alignment of the TIR domains of human and mouse TICAM-1, Mal (TIRAP), and MyD88 was performed, so as to compare the aligned TIR domains.

The TIR domain (from 394-position to 532-position) of human TICAM-1, TIR domain (396-position to 534-position) of mouse TICAM-1, TIR domain (160-position to 296-position) of human MyD88 (accession No. U70451), and TIR domain (85-position to 216-position) of human Mal/TIRAP (accession No. AF406652) were aligned using Clustal W. The regions of the TIR domains were presumed using SMART program. Results of alignments are illustrated in FIG. 6.

Again in FIG. 6, "TICAM-1.hu" indicates human TICAM-1, while "TICAM-1.mu" indicates mouse TICAM-1. Asterisk (*) indicates identical residues, while double dots (:) indicates conserved substitutions, and single dot (•) indicates semi-conversed substitutions. For details of Boxes 1 to 3, please refer to the Documents mentioned above.

Example 6

Detection of TICAM-1

Expression of mRNA of TICAM-1 in various human tissues was examined by Northern blotting by using a Northern blot kit (made by Clontech). That is, mRNA extracted from various human tissues were electrophoresed under denaturing condition, using humane 12-lane "Human MTN Blot" membranes and "Blot It" membranes (made by Clontech).

Patterns of the electrophoresis were transferred to filters and hybridized under stringent conditions using C-terminal TICAM-1 probe ($^{32}$P-labeled 1406 to 2193 bases of cDNA encoding human TICAM-1). The filters were exposed for 1 day using an image analyzer "BAS2000" (made by Fujifilm), thereby to develop the patterns. Results are given in the upper panel of FIG. 7.

Similar operation was performed using labeled β-actin probe as control. Patters on filters were developed by 4-hour exposure. Results are given in the lower panel in FIG. 7.

Figure 7:
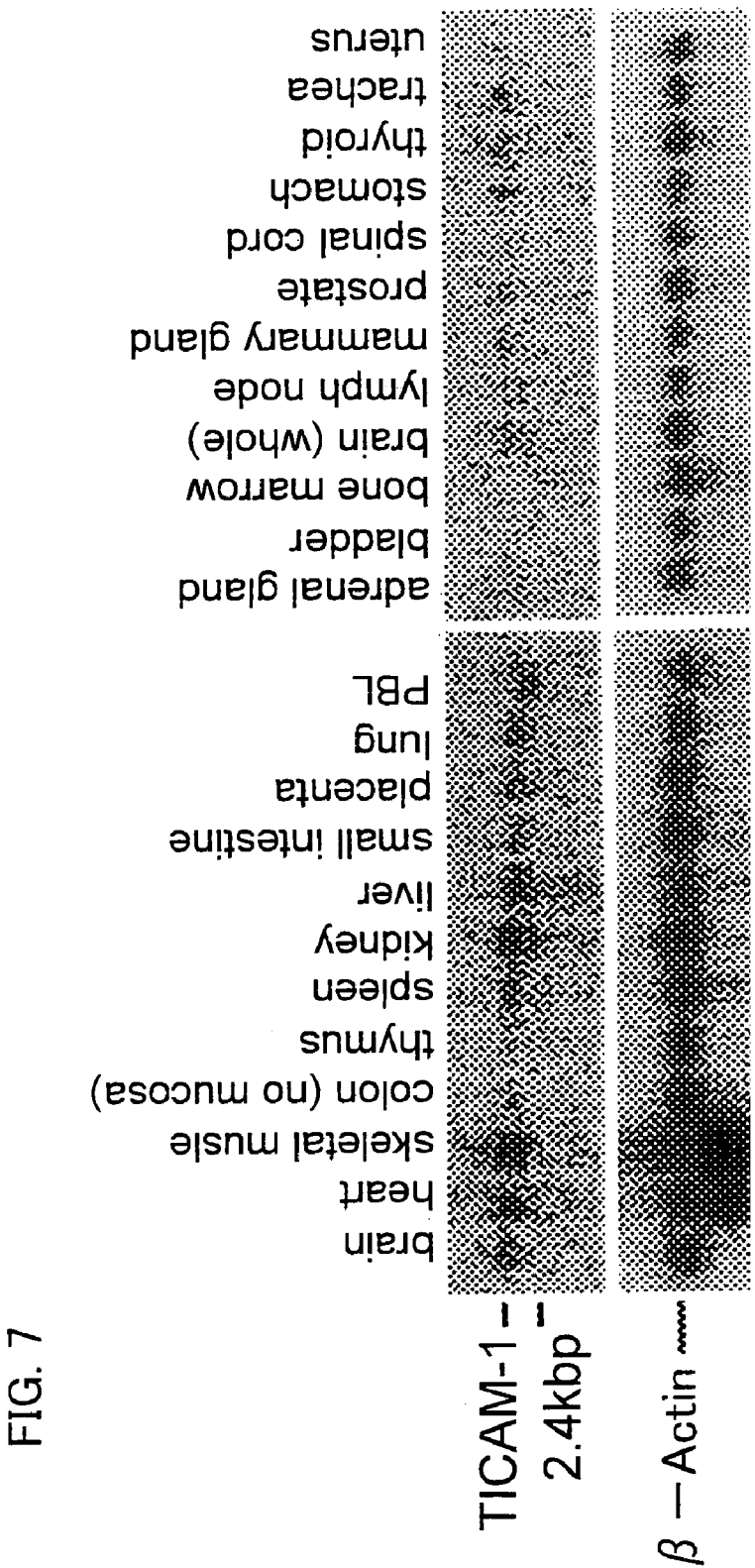
FIG. 7 is a view illustrating expression of mRNA of TICAM-1 in various human tissues.

As illustrated in FIG. 7, mRNA of 2.6 kilo bases (kb) of human TICAM-1 was detected in most of the tissues encompassing peripheral blood leukocyte (PBL), brain, spleen, thymus, liver, lung, kidney, skeletal muscle, heart, and placenta, and others.

Example 7

Detection of TICAM-1 Using RT-PCT

Figure 8:
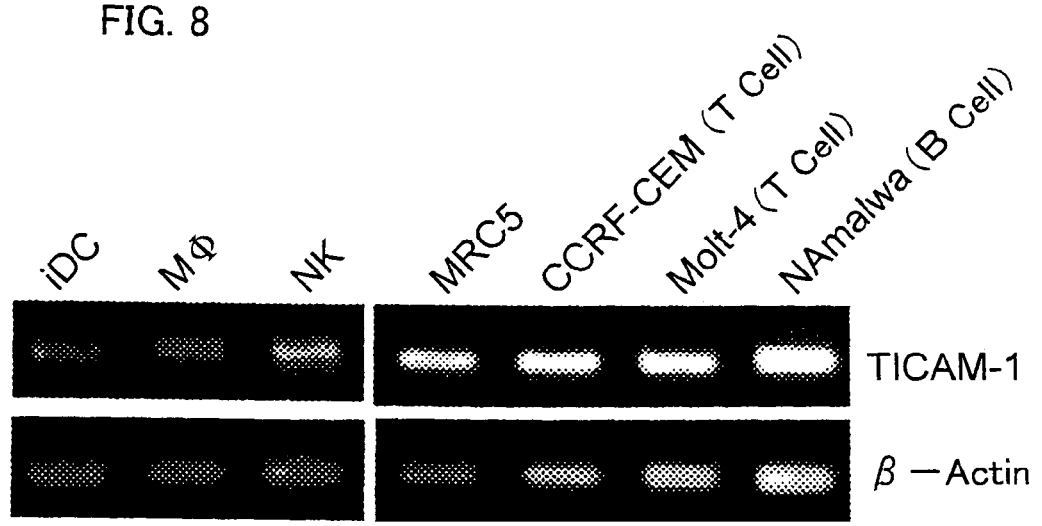
FIG. 8 is a view illustrating results of detection of mRNA of TICAM-1 in various types of human cells and human cell lines by RT-RCR.

Total RNA was isolated from plural kinds of the human cells and human cell lines indicated in FIG. 8. Then RT-PCR was performed with the total RNA and primers for human TICAM-1. 35 PCR cycles were carried out.

In FIG. 8, "Mf" denotes microphages, while iDC denotes immature dendritic cells. "−" denotes the control without template. Moreover, 20-cycle PCR was performed using β-actin primer as control.

All of the immature dendritic cells (iDC), microphages (MΦ), and NK (natural killer) cells, each of which were prepared from human peripheral blood, expressed mRNA of human TICAM-1 (FIG. 8). Moreover, mRNA of human TICAM-1 was positive in cell lines of lymphoid lineage (T cell CCRF-CEM, T cell Molt-4, B cell Namalwa) and fibroblasts (MRC5).

Summarizing these results, it was deduced that the expression of human TICAM-1 is ubiquitous and weak compared with the expression of β-actin.

Example 8

Investigation of Interaction Between TICAM-1 and TLR3 by Immunoprecipitation

Association of TIR domain of human TLR3 with TICAM-1 was confirmed by immunoprecipitation in HEK293 cells expressing (flag-tagged) human TLR3 and (HA-tagged) human TICAM-1.

Firstly, HEK293 cells were transiently transfected in 6-well plates using Lipofectamine 2000 reagent with 3 μg of human TLR3-Flag expression vector (flag-tagged TICAM-1 expression vector) and 0.5 μg of TICAM-1-HA expression vector (HA-tagged TICAM-1 expression vector). A total amount of DNA was kept constant (4 μg) by adding empty vector.

Twenty four hours after the transfection, the cells were stimulated for 15 min with medium alone (lanes 1 and 3 in FIG. 9), or with 10 μg/ml of poly(I:C) (lanes 2 and 4 in FIG. 9), and then lysed with a lysis buffer (pH 7.5; containing 25 mM of Tris, 150 mM of NaCl, 1 wt % of NP-40, 2 mM of PMSE, 25 mM indoacetoamindo, 10 mM of EDTA).

After centrifugation, cell lysates were incubated at 4° C. for 2 hours together with an immunoprecipitation probe (IP), that is, mouse IgG1 (lanes 1 and 2 in FIG. 9) or anti-Flag M2 antibody (lanes 3 and 4; made by Sigma), and subjected to immunoprecipitation. For control reaction, mouse IgG1 was used. Immune complexes were precipitated with protein G-Sepharose. Precipitants were washed well.

Then, to elute protein thus immunoprecipitated, the precipitants were boiled with DPBS containing 1 wt % SDS, 0.2 wt % of NP-40, and 5 wt % of 2-mercaptoethanol. Next, eluates were immunoblotted using anti-Flag antibody or anti-HA antibody, and then subjected to SDS-PAGE. The lysates were also immunoblotted in order to investigate expression of the transfected TICAM-1-HA.

Figure 9:
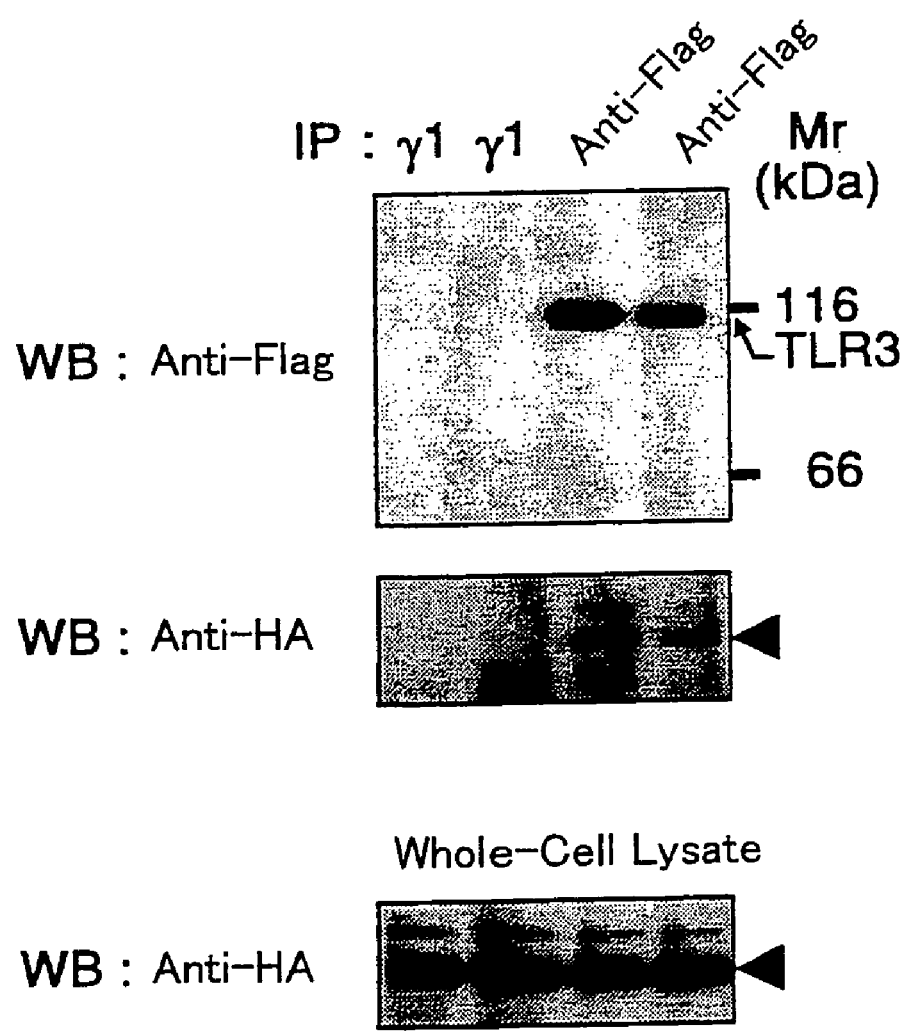
FIG. 9 is a view illustrating results of immunoprecipitation for analyzing interaction between human TICAM-1 and human TLR3.

Results (western blot; WB) are illustrated in FIG. 9. In FIG. 9, "+" denotes that the transfection or stimulation was performed, whereas "−" denotes that the transfection or stimulation was not performed. The middle panel illustrates part of the Western blot (immune blot) of the cell lysates. The lower panel is the Western blot of the whole cell lysates.

As illustrated in FIG. 9, the molecular complex containing both human TLR3 and human TICAM-1 was detected using anti-Flag antibody by immunoprecipitation (lanes 3 and 4 in FIG. 9; the position indicated by the arrow in the upper panel). Therefore, it was confirmed that human TICAM-1 associates with human TLR3.

Moreover, under the presence of a specific monoclonal antibody TLR3.7 against human TLR3 (c.f. Non-Patent Document), similar association of human TLR3 with human TICAM-1 was confirmed (not illustrated). Moreover, the stimulation of the human TLR3-expressing cells by poly(I:C) had almost no effect on the molecular association (FIG. 9).

The Western blot (WB) of the whole cell lysates showed the expression of TICAM-1-HA (at the position indicated by the arrow in the middle panel). By the Western blot of the whole cell lysates detected a high-molecular-mass form above the major band of human TICAM-1 was also detected (upper panel in FIG. 9). This high-molecular-mass form presumably represents a phosphorylated form.

Figure 10:
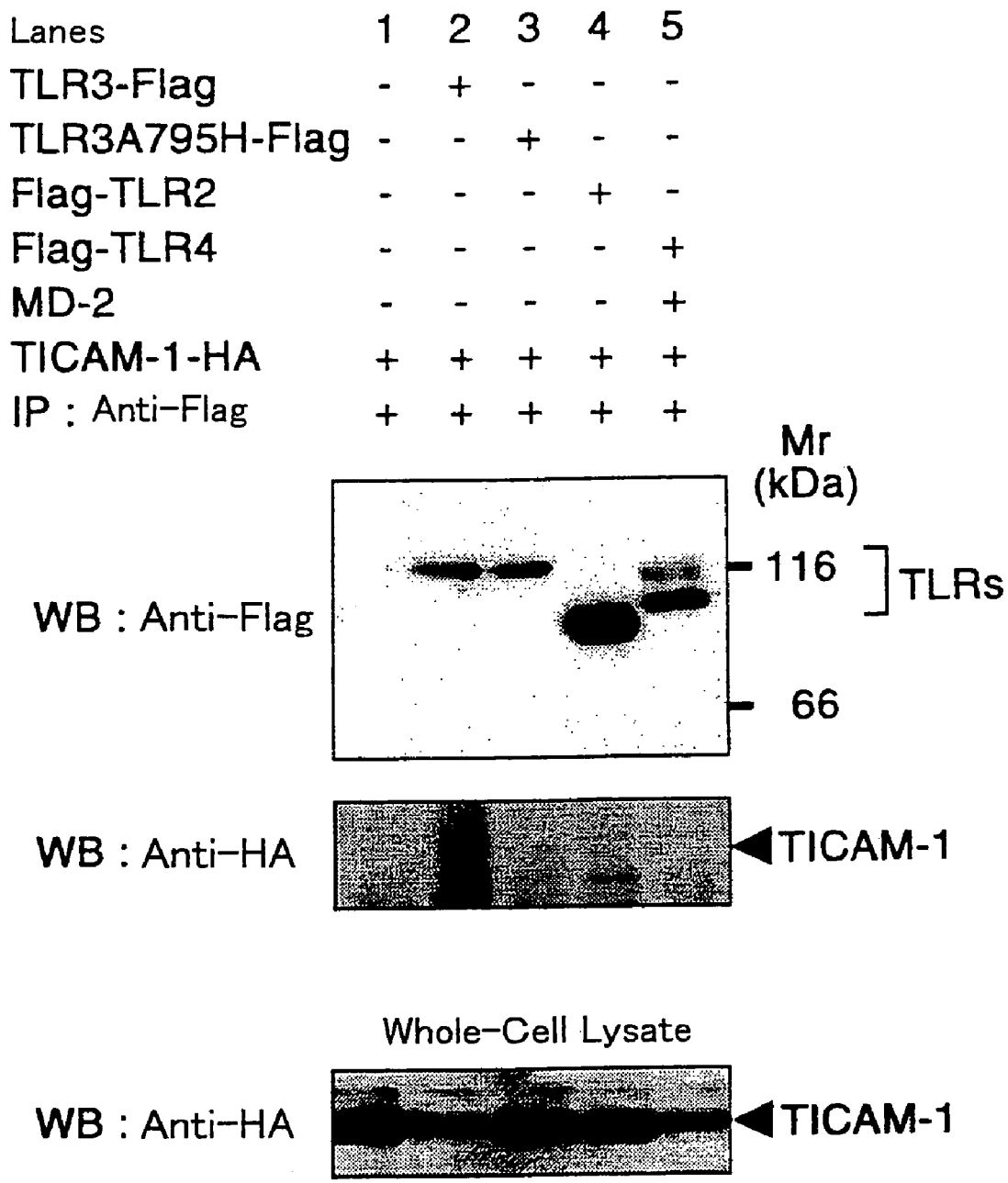
FIG. 10 is a view illustrating results of immunoprecipitation for analyzing interaction between human TICAM-1 and a human TLR other than human TLR3, or a human TLR3 mutant.

Next, it was investigated whether TICAM-1 binds to other TLR and TLR3 mutant under the same conditions (FIG. 10).

Firstly, HEK293 cells was transiently transfected with human TICAM-1-HA (0.05 μg) and (1) empty vector (4 μg), (2) human TLR3-Flag expression vector (3 μg), (3) TLR3A795H-Flag expression vector (3 μg), (4) Flag-TLR2 expression vector (2 μg), (5) Flag-TLR4 expression vector (2 μg), or (6) MD-2 expression vector (1 μg). A total amount of DNA was kept constant (4 μg) by adding empty vector. Twenty four hours after the transfection, the cells were lysed with lysis buffer.

Lysates were immunoprecipitated with mouse IgG1 (not illustrated) or anti-FlagM2 antibody (lanes 1 to 5), and then boiled with DPBS containing 1 wt % of SDS, 0.2 wt % of NP-40, and 5 wt % of 2-mercaptoethanol, thereby to elute immunoprecipitated protein. Next, elutes were immunoblotted with the anti-Flag antibody or anti-HA antibody and then subjected to SDS-PAGE. The lysates were also immunoblotted in order to investigate expression of the transfected TICAM-1-HA. Immunoblotting was performed with the anti-flag antibody or anti-HA antibody.

FIG. 10 illustrates results thus obtained. In the table, "+" denotes that the transfection was performed, while "−" denotes that the transfection was not performed. In the upper panel of FIG. 10, the immunoprecipitated and Flag-tagged TLR protein is illustrated. In the middle panel, TICAM-1 interacting with wild-type TLR3 (parenthesis or arrow; only lane 2 is illustrated). In the lower panel of FIG. 10, the transfected TICAM-1-HA (arrow) is illustrated.

As illustrated in FIG. 10, human TLR3 was coprecipitated with human TICAM-1, but not with TLR3 mutant A795H, TLR2, and TLR4. That is, A795H TLR3 mutant lost the ability of binding to TICAM-1 (c.f. FIG. 10). TLR2 and TLR4 could not be coprecipitated with TICAM-1 even when they are coexpressed with MD-2 (c.f. FIG. 10). These results were confirmed in the case where the monoclonal antibody against TLR 2 or the monoclonal antibody against TLR4 was used (not illustrated).

These results confirmed that human TICAM-1 specifically binds to human TLR3.

Moreover, together with the results of the yeast two-hybrid analysis and specificity confirmation in the experiments using the monoclonal antibodies for TLR2, TLR3, and TLR4, it was concluded that in human cells, the TIR domain of human TLR3 can associate with the adaptor protein TICAM-1, but TLR2 and TLR4 cannot associate with the adaptor protein TICAM-1.

Example 9

Expression Vector Preparation of Human TICAM-1 and its Mutant

Figure 11:
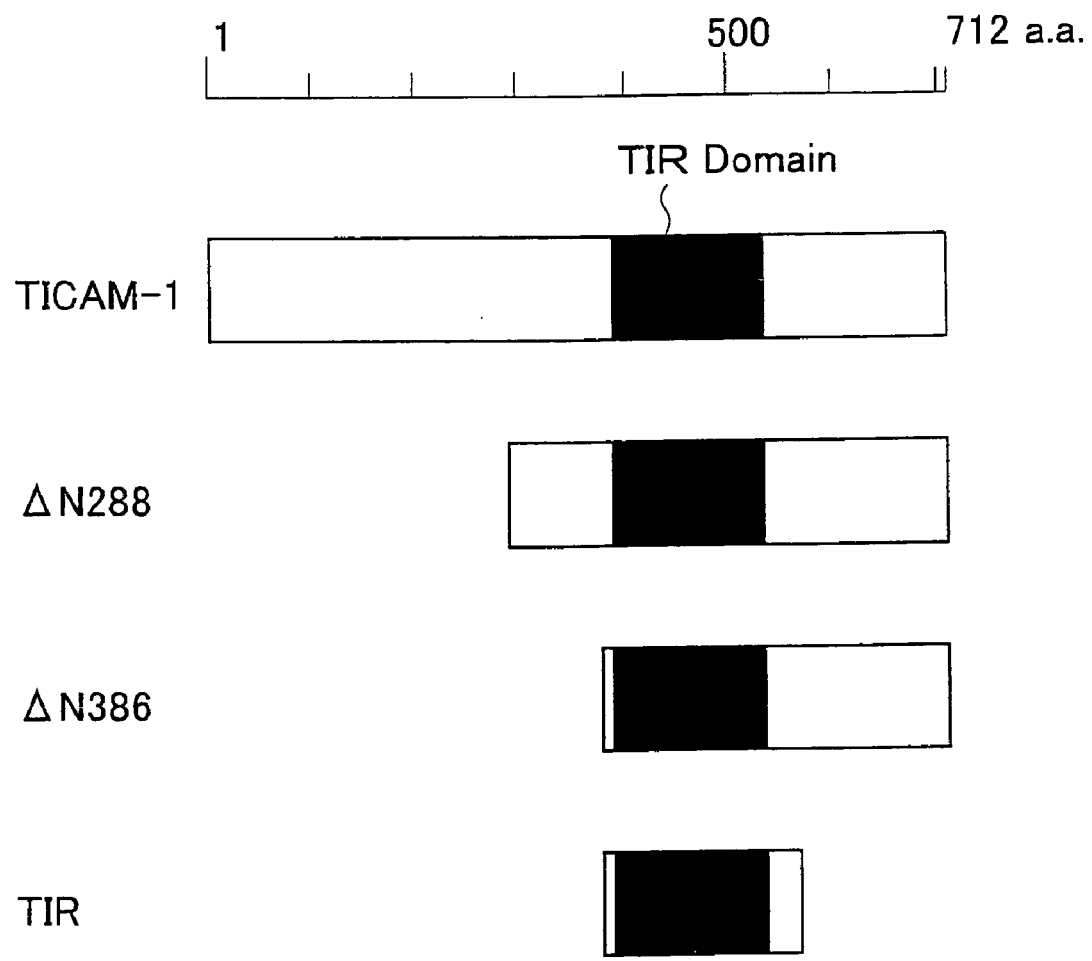
FIG. 11 is a view illustrating a mutant of human TICAM-1.

As illustrated in FIG. 11, expression vector for human TICAM-1 and three types of expression vectors respectively encoding its three types of mutants were prepared. The three types of mutants are: a mutant in which an amino acid sequence ranging from 1-position to 288-position of human TICAM-1 is deleted (hereinafter, this mutant is called "human TICAM-1 (ΔN288)"); a mutant in which an amino acid sequence ranging from 1-position to 386-position of human TICAM-1 is deleted (hereinafter, this mutant is called "human TICAM-1 (ΔN386)"); and a mutant which is made of almost only TIR domain of human TICAM-1 (hereinafter, this mutant is called "human TICAM-1•TIR"). The mutant which is made of almost only TIR domain of human TICAM-1 (human TICAM-1•TIR) was more specifically a mutant in which an amino acid sequence ranging from 1-position to 386-position and an amino acid sequence ranging from 557-position to 712-position of human TICAM-1 were deleted, that is, a mutant protein made of an amino acid sequence ranging from 387-position to 556-position of the amino acid sequence constituting human TICAM-1.

Human TICAM-1 Expression vector was prepared by placing the full-length cDNA encoding TICAM-1 into XhoI-NotI site of the plasmid vector pEFBOS. pEFBOS-TICAM-1 (ΔN288), pEFBOS-TICAM-1 (ΔN386), and pEFBOS-TICAM-1 (TIR) were respectively prepared by inserting, into the XhoI-NotI site of the plasmid vector pEFBOS, (i) an amino acid sequence ranging from 289-position to 712-position, (ii) an amino acid sequence ranging from 387-position to 712-position, and (iii) an amino acid sequence ranging from 387-position to 556-position; (i), (ii) and (iii) are regions of the human TICAM-1 following the Kozack sequence and the first ATG. The plasmid vectors were prepared by using "Plasmid Maxi" kit (made by Qiagen) containing no endotoxin.

Example 10

Functional Analysis Caused by Mutation of Human TICAM-1

To investigate function of human TICAM-1, reporter gene assay to measure the level of NF-κB activation and interferon β activation was performed for human TICAM-1 and its mutant. That is, functional binding of TICAM-1 to the interferon β promoter and the other was tested in HEK293 cells.

By using gene transfecting cationic lipid "Lipofectamine 2000" reagent (made by Gibco), the HEK 293 cells in 24-well plates ($2 \times 10^5$ cells per well) were transfected with (i) 0.1 µg of luciferase-linked NF-κB reporter gene (made by Stratagene) (c.f. 12(b)) or 0.1 µg of p125Luc reporter plasmid (c.f. 12(a)), and (ii) empty vector, human TICAM-1 TIR, human TICAM-1 (ΔN386), human TICAM-1 (ΔN288), or the vector expressing the full-length human TICAM-1 (10 ng or 100 ng respectively). A total amount (0.8 µg to 1.0 µg) of transfected DNA was adjusted by adding the empty vector. Moreover, plasmid vector pCMV β (made by Clontech; 5 ng) was used as internal control.

Twenty four hours after the transfection, the cells were lysed with lysis buffer (made by Promega). Luciferase activity in thus prepared lysates were measured according to the manufacturer's instructions, the luciferase activity indicating level of NF-κB activation caused by stimulation after the transfection. Moreover, the experiment was performed three times. Representing values were considered as measurement values. Level of the interferon β activation is illustrated in FIG. 12(a), and that of the NF-κB activation is illustrated in FIG. 12(b).

Significant enhancement of the interferon β promoter activation was observed in the HEK293 cells in which the small amount (0.1 µg) of the full-length human TICAM-1 was expressed (see FIG. 12(a)). Chromosome deletion analysis of FIGS. 12(a) and 12(b) suggested that the TIR domain derived from human TICAM-1 had the function described above, unlike TIR of MyD88, which served as dominant-negative. Ligation of N-terminal region and C-terminal region to the TIR domain enhanced the interferon β promoter activation (see FIG. 12(a)). This suggested that the TIR domain of human TICAM-1 is a minimal essential element sufficient to activate the interferon β promoter by causing the tail of human TLR3 to bind to downstream molecule.

Moreover, the result of a similar transfection experiment to test the ability of human TICAM-1 to activate NF-κB showed that the full-length TICAM-1 activates NF-κB promoter to lesser extent than the interferon β promoter. The mutant lacking the N-terminal domain showed a greater ability to activate NF-κB than the cells having TIR domain or the full-length TICAM-1 (see FIGS. 12(a) and 12(b)). Therefore, it is considered that the N-terminal sequence direct a strong preference for the interferon β production on the transfectant, and relatively suppress the NF-κB activation at the same time. Moreover, the C-terminal domain slightly enhanced both of interferon β activation and NF-κB activation (see FIGS. 12(a) and 12(b)).

Further, in the cell expressing the full-length human TICAM-1, the interferon β promoter activation was induced without transfection of TLR3 in some cases (see FIGS. 12(a) and 12(b)).

This suggested that human TICAM-1 spontaneously activates interferon β promoter, thereby to induce the interferon β production.

The spontaneous induction of the interferon β production is ascribed to homo-dimerization or complex formation of human TICAM-1 with an unknown molecule. This finding result is consistent with those about Mal that tends to auto-dimerize, and with structural analysis result of TIR domain of the adaptor molecule MyD88, which also tends to auto-dimerize.

Example 11

Analysis of TLR3-Mediated Signaling

Next, a reporter gene assay was carried out to analyze the human TLR3-mediated signaling. Specifically speaking, the TIR domain (minimal essential constituent of TICAM-1) was used in HEK293 cells to test whether the effect of TLR3 and/or poly(I:C) on the interferon β promoter activation is additive.

Firstly, a dominant-negative mutant of human TICAM-1•TIR was prepared by inserting dot mutation into the human TICAM-1•TIR expression vector (pEFBOS-TICAM-1 (TIR)), the dot mutation replacing amino acid 434 (proline) with histidine.

Figure 13:
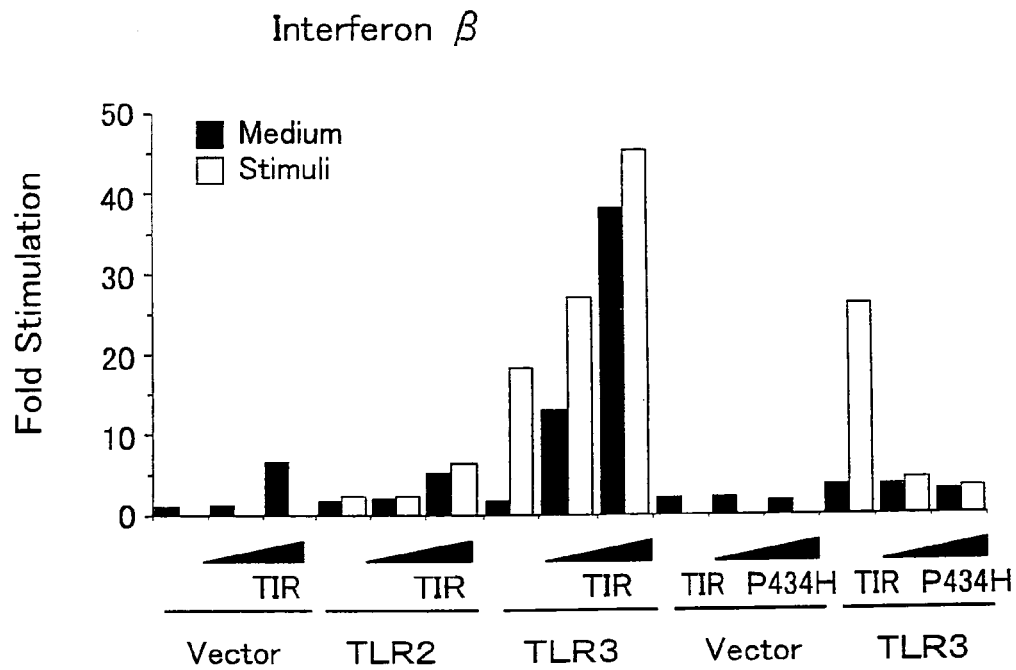
FIG. 13(a) is a view illustrating measurement results of interferon β activation by the reporter gene expression for analyzing the signaling mediated by TLR3.
FIG. 13(b) is a view illustrating measurement results of NF-κB activation by the reporter gene expression for analyzing the signaling mediated by TLR3.
Figure 13:
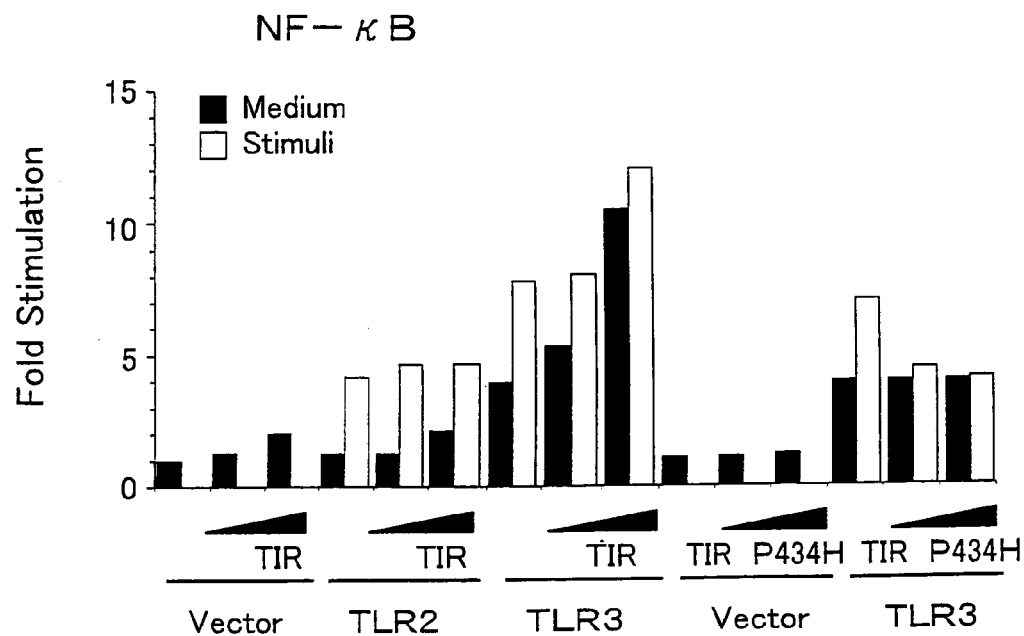

By using the gene transfecting cationic lipid "Lipfectamine 2000" reagent (made by Gibco), HEK293 cells in 24-well plates were transfected with (i) 0.1 μg of luciferase-linked NF-κB reporter gene (made by Stratagene) (c.f. FIG. 13(b)) or 0.1 μg of p125•luc reporter plasmid (c.f. FIG. 13(a)), (ii) TICAM-1•TIR (0.1 ng and 10 ng) or a plasmid (0, 0.2 μg, 0.6 μg), the plasmid encoding TICAM-1•TIR mutant TIR•P434H of TICAM-1 TIR, and (iii) empty vector, TLR2 (0.1 μg), or TLR3 (0.6 μg).

A total amount (0.8 μg to 1.0 μg) of transfected DNA was adjusted by adding the empty vectors. Moreover, plasmid vector pCMVβ (made by Clontech; 5 ng) was used as an internal control.

Twenty four hours after the transfection, the cells were stimulated for 6 hours with 100 nM of MALP-2 (TLR2 stimulation) or 10 μg/ml of poly(I:C) (TLR3 stimulation), and then lyzed with the lysis buffer (made by Promega). Luciferase activity that indicate the interferon β activation or NF-κB activation caused by stimulation after the transfection in thus prepared lysates were measured according to the manufacturer's instructions. This experiment was repeated three times. Representing values thereof were considered as measurement values. Level of the interferon β activation is illustrated in FIG. 13(a), and level of the NF-κB activation is illustrated in FIG. 13(b).

The transfection of TLR3 and TIR of TICAM-1 resulted in strong interferon β promoter activation (see, FIGS. 13(a) and 13(b). Moreover, as clearly shown in the results of low-dose TICAM-1 TIR transfectants (see FIGS. 13(a) and 13(b)), the poly(I:C) stimulation of the transfectant enhanced the TICAM-1 mediated interferon β promoter activation. It was observed that NF-κB activation was enhanced by human TLR3 co-transfection and poly(I:C) stimulation of the cell expressing human TICAM-1 (see FIGS. 13(a) and 13(b)). On the other hand, the activation of NF-κB did not occur in response to the human TLR2 stimulation, even if the cells expressing human TLR2 were additionally transfected with TICAM-1 (see FIGS. 13(a) and 13(b)). This indicates that human TICAM-1 is specific for human TLR3. Moreover, TLR2 coexpressed with TIR of TICAM-1 in HEK293 did not activate the expression of interferon β promoter even in the cells stimulated with mycoplasma lipopeptide MALP-2, which is a human TLR2 ligand.

This indicates that the functional association of human TLR3 with human TICAM-1 relates to the poly(I:3)-mediated activation of interferon β promoter.

Moreover, it was noted with interest that the poly(I:C)-TLR3-mediated activations of the interferon β promoter and NF-κB were completely cancelled by transfecting with the dominant-negative mutant P434H in lieu of the activating TICAM-1 TIR, the dominant-negative mutant P434H being a mutant of TICAM-1 TIR. This canceling is presumably because the dominant-negative mutant P434H had the ability of binding to human TLR3 but lost the ability of inducing the interferon β production. Thus, this mutant rather blocks the human TLR3-mediated signaling thereby to inhibit the interferon β production.

Example 12

Functional Analysis of Adaptor Molecule

Next, a reporter gene assay was carried out to compare human TICMA-1, the known adaptor molecule MyD88, and Mal/TIRAP in terms of levels of interferon β and NF-κB activations.

Figure 14:
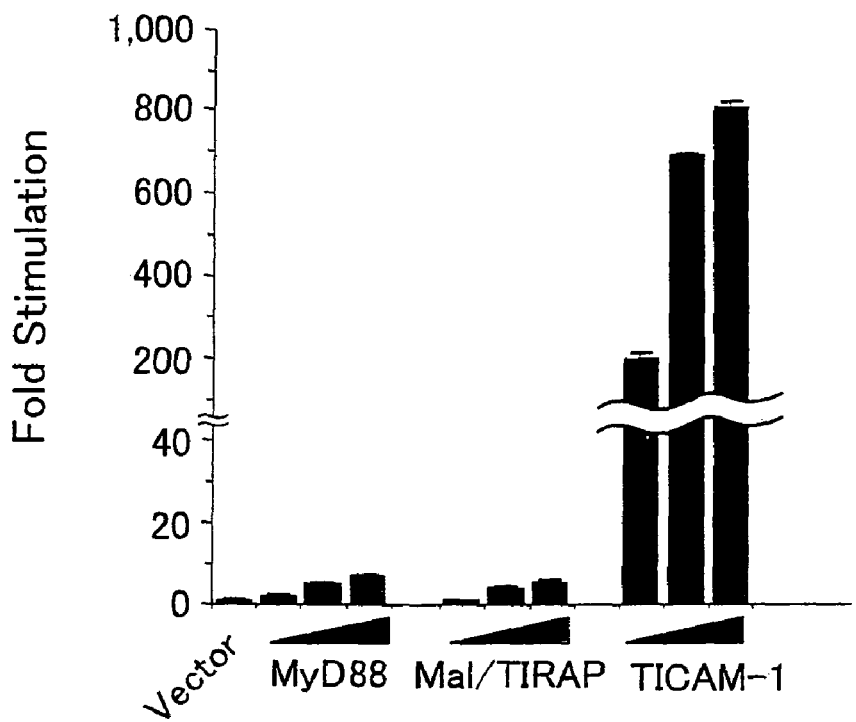
FIG. 14(a) is a view illustrating results of interferon β activation caused by human TICAM-1 and a known adaptor molecule.
FIG. 14(b) is a view illustrating measurements result of NF-κB activation caused by human TICAM-1 and the known adaptor molecule.
Figure 14:
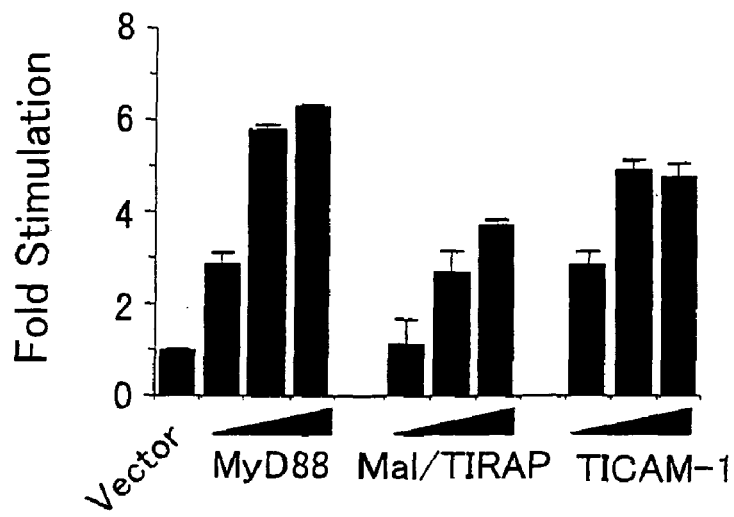

By using the gene transfecting cationic lipid "Lipfectamine 2000" reagent (made by Gibco), HEK293 cells on 24-well plates were transfected with (i) 0.1 μg of luciferase-linked NF-κB reporter gene (made by Stratagene) (c.f. FIG. 14(b)) or 0.1 μg of p125 luc reporter plasmid (c.f. FIG. 14(a)), (ii) empty vector, MyD88, Mal/TIRAP, or the full-length TICAM-1 (respectively 10, 100, or 200 ng).

A total amount (0.8 μg to 1.0 μg) of transfected DNA was adjusted by adding the empty vectors. Moreover, plasmid vector pCMVβ (made by Clontech; 5 ng) was used as an internal control.

Twenty four hours after the transfection, the cells were lysed with the lysis buffer (made by Promega). The interferon β activity or Luciferase activity in the lysates were measured according to the manufacturer's instructions, the luciferase activity indicating interferon β or NF-κB activation. This experiment was repeated three times, and representing values were considered as measurement values. Level of the interferon β activation is illustrated in FIG. 14(a) and level of the interferon activation of NF-κB is illustrated in FIG. 14(b). The comparison between activation profiles of interferon β promoter and NF-κB (FIGS. 14(a) and 14(b)) showed that these three adaptor molecules induced similar levels of NF-κB activation (FIGS. 14(a) and 14(b)), but induction of interferon β promoter activation by the full-length human TICAM-1 was more than 100-fold stronger than that by the adaptor molecule Mal/TIRAP or MyD88, without any additional stimulation such as TLR3 and/or poly(I:C) (FIGS. 14(a) and (14(b)). This suggested that human TICAM-1 can significantly enhanced the interferon β production by directly acting on the interferon β promoter.

Example 13

Western Blot

HEK293 cells were transiently transfected with plasmids (100 ng) respectively encoding the adaptor molecule Mal-HA, MyD88-HA, and TICAM-1-HA. 24 hours after the transfection, the cells were lysed. Expressed proteins were analyzed by Western blotting with anti-HA antibody.

Figure 15:
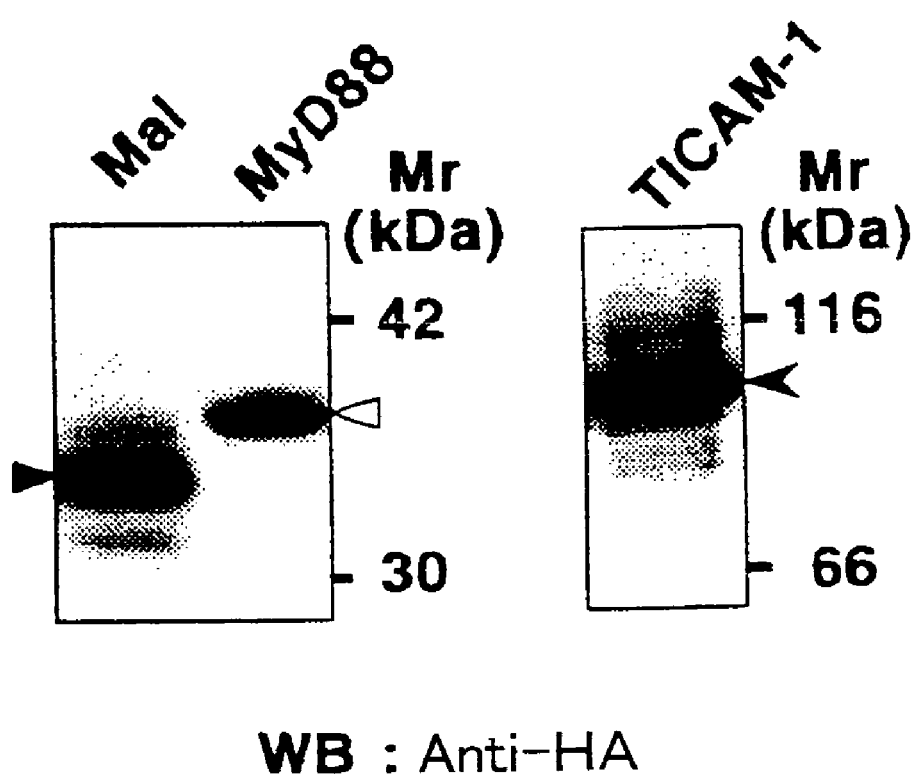
FIG. 15 is a view illustrating results of western blot that indicated expression of human TICAM-1 and the known adaptor molecule in HEK293 cells.

Thus obtained western blot is illustrated in FIG. 15. The black arrow on the left indicates the expression of Ma1-HA, the empty arrow in middle indicates the expression of MyD88-HA, and the arrow on the right indicates the expression of TICAM-1-HA. The results illustrated in FIG. 15 confirmed that these adaptor molecules had appropriate levels of protein expression.

Example 14

TICAM-1 Knockdown

Next, to confirm the signaling to cause TICAM-1-medicated induction of interferon β production, human TICAM-1 knockdown cells were produced by transfection using single-stranded RNA.

Figure 16:
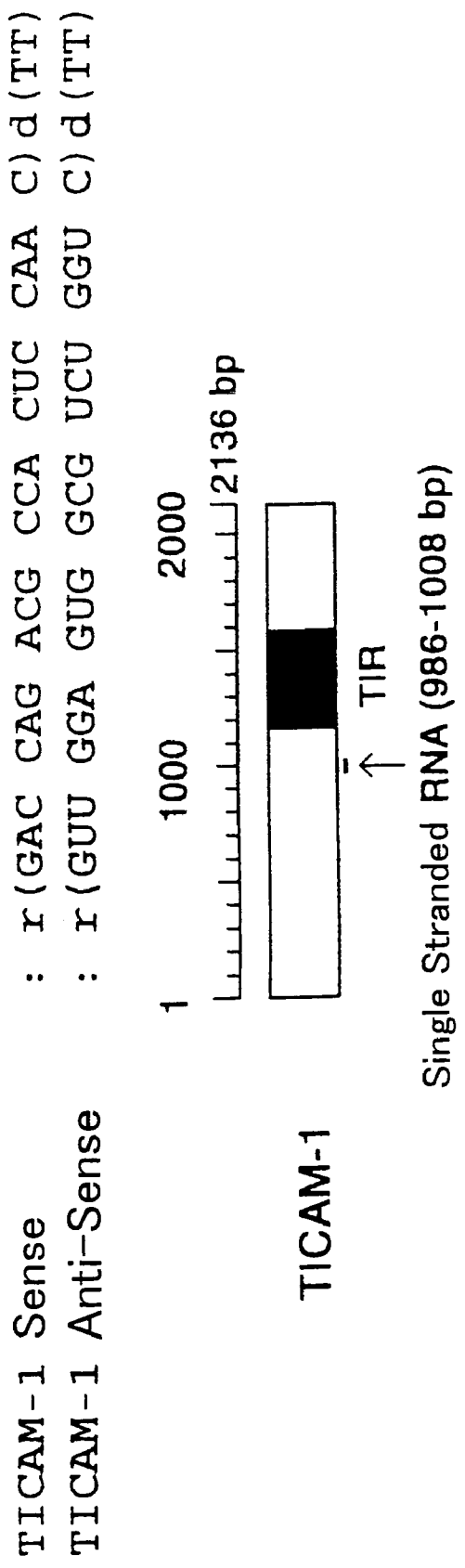
FIG. 16 is a view illustrating a sequence of single-stranded RNA of human TICAM-1. The ribonucleotide sequences are shown for the sense (SEQ ID NO: 5) and antisense (SEQ ID NO: 6) strands of RNA.

The single-stranded RNA of human TICAM-1 is illustrated in FIG. 16: sense is r[GACCAGACGCCACUCCAAC] (SEQ ID NO: 5) d[TT], while antisense is r[GUUGGAGUG-GCGUCUGGUC] (SEQ ID NO: 6) d[TT] (TICAM-1). Here, "r" and "d" respectively denote ribonucleotide and deoxyribonucleotide. The single-stranded RNA region in the message of TICAM-1 is given under the single-stranded RNA sequence.

The location of the single stranded RNA in the human TICAM-1 message effective for gene silencing is positioned at 986 to 1008 bases (bp), as shown in FIG. 6.

HeLa cells and MRC-5 cells expressed TLR3 on cell surface and produced interferon β in response to exogenously added poly(I:C). Both of them contained mRNA of TICAM-1 and TLR3 (data not shown). In the cells in which the single-stranded RNA is transfected in the position, the production of interferon β is partly reduced.

Example 15

RT-PCR

Figure 17:
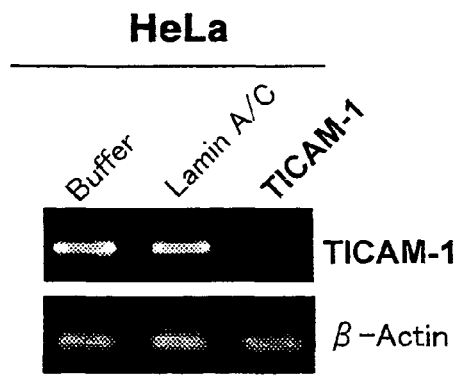
FIGS. 17(a) and 17(b) are views illustrating results of RT-PCR analysis.
Figure 17:
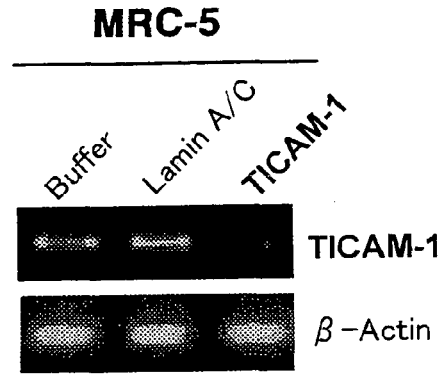

RT-PCR analysis was carried out with the primer for human TICAM-1 or the primer for β-actin. Results are given in FIGS. 17(a) and 17(b). FIG. 17(a) is for HeLa cells, and FIG. 17(b) is for MRC-5 cells.

The primer for human TICAM-1 had the following sequence:

```
5'-CCAGATGCAACCTCCACTG    (5' primer, SEQ ID NO: 7)
G-3'
and

5'-TGGAGGAAGGAACAGGACAC   (3' primer, SEQ ID NO: 8).
C-3'.
```

In the HeLa cells and MRC-5 cells, mRNA level of human TICAM-1 was suppressed by approximately 80% by RNAi (RNA interference) method (FIGS. 17(a) and 17(b)).

These tests directly proved that TICAM-1 is the adaptor molecule that links (i) TLR3 activation mediated by double-stranded RNA and (ii) the interferon β production.

Example 16

RNAi

It was investigated whether or not supplementation of double-stranded RNA induces the interferon β protein production in TCAM-1-deleted HeLa cells and MRC-5 cells.

Using "Oligofectamine (made by Invitrogen; final concentration 200 nM), HeLa cells or MRC-5 cells were transfected with (i) buffer only, (ii) single-stranded RNA of Lamin A/C (Control; final concentration 200 nM), or (iii) single-stranded RNA of human TICAM-1. 48 hours from the transfection, HeLa cells and MRC-5 cells were stimulated respectively with 50 μg/ml and 10 μg/ml of poly(I:C).

Figure 18:
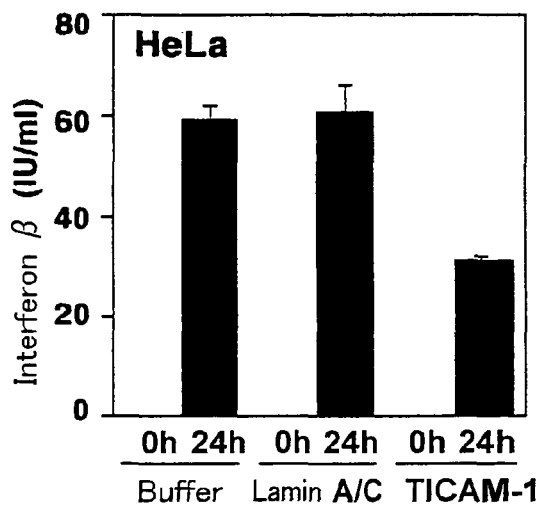
FIGS. 18(a) and 18(b) are views illustrating results of analysis by RNAi.
Figure 18:
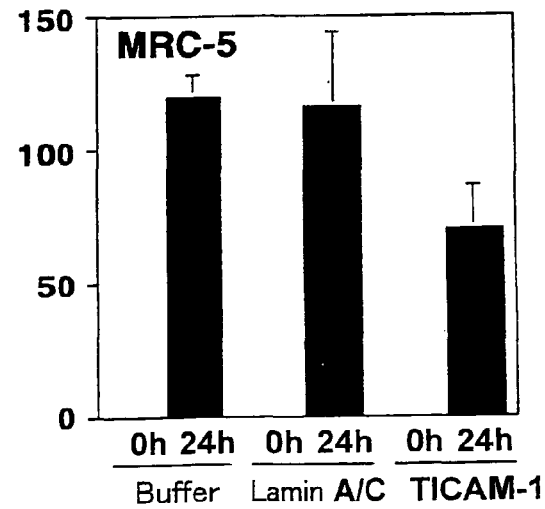

Interferon β concentration of supernatants before 24-hour stimulation (i.e., after 0-hour stimulation) and after 24-hour stimulation were measured by ELISA. FIG. 18(a) illustrates measurement results of HeLa cells, and FIG. 18(b) illustrates measurement results of MRC-5 cells.

Basic method of RNAi was described in Elbashir et al. (Duplexes of 21-nucleotide RNAs mediate RNA interference in cultured mammalian cells, Nature 411: 494-498, 2001). Moreover, its detailed procedure and conditions are described in Oshiumi et al. (RNA interference for mammalian cells, Folia Pharme, Jpn. 120: 91-95, 2002).

The single-stranded RNA of human TICAM-1 had the sequence whose sense is r[GACCAGACGCCACUCCAAC] (SEQ ID NO: 5) d[TT] and antisense is r[GUUGGAGUG-GCGUCUGGUC] (SEQ ID NO: 6) d[TT] (TICAM-1). Moreover, single-stranded RNA of lamin A/C has the sequence whose sense is r[CUGGACUUCCAGAAGAACA] (SEQ ID NO: 9) d[TT] and antisense is r[UGUUCUUCUG-GAAGUCCAG] (SEQ ID NO: 10) d[TT]. Here, "r" and "d" respectively denote ribonucleotide and deoxyribonucleotide. The single-stranded RNA region in the message of TICAM-1 is given under the single-stranded RNA sequence. These single-stranded RNAs were purchased from Xeragon Inc. (USA).

Cells (HeLa cells or MRC-5 cells) stimulated with poly(I:C) (10 μg/ml or 50 μg/ml) were cultured for 24 hours (24 h), and supernatants were collected. Human interferon β concentrations in the supernatants from the culture supernatants were measured by ELISA (Enzyme Linked Immunosorbent Assay; TEB) Results are illustrated in FIGS. 18(a) and 18(b).

In these cells, the level of interferon β production was specifically inhibited by single-stranded RNA to approximately 50% (FIGS. 18(a) and 18(b)).

Therefore, these experiments proved that TICAM-1 is an adaptor molecule that links the double-stranded RNA-mediated TLR3 activation and the interferon β production.

INDUSTRIAL APPLICABILITY

As described above, the present invention relates to a novel protein that induces type I interferon production by specifically binding to mammalian Toll-like receptor 3, and its mutants, a gene of the protein, a recombinant expression vector containing the gene, an antibody against the protein. As described above, the prevent invention is useful for (i) studying and analyzing the TLR3-mediated signaling system and its control mechanism, (ii) pathological analysis on various diseases to which the signaling system and its control mechanism involve, (iii) prevention and therapy of viral infectious diseases such as hepatitis B, hepatitis C, and the like, (iv) therapy of tumors, (v) therapy of autoimmune diseases, (vi) therapy of atopic diseases, (vii) and other usages. Therefore, the present invention is expected to contribute to medical care development such as various pharmaceutical industries.

We claim:

1. A method for inducing interferon β production in an isolated mammalian cell, the method comprising transfecting the isolated mammalian cell in which a Toll-like receptor 3 is naturally expressed with a vector containing a DNA molecule encoding a protein that binds to the Toll-like receptor 3, wherein the protein is comprised of the amino acid sequence of SEQ ID NO: 2 or from position 394 to position 532 of SEQ ID NO: 2 and wherein binding of the protein to the Toll-like receptor 3 induces interferon β production in said mammalian cell.

2. The method according to claim 1, wherein the isolated mammalian cell is a human fibroblast, a human dendritic cell, a human intestinal epithelial cell, or a mouse fibroblast.

3. The method according to claim 1, wherein the DNA molecule has the nucleotide sequence from position 1242 to position 1658 of SEQ ID NO: 1.

4. A therapeutic method for treating cancer, the method comprising enhancing interferon β production by administering an isolated cell transfected with a vector containing a DNA molecule encoding a protein comprised of the amino acid sequence of SEQ ID NO: 2 or from position 394 to position 532 of SEQ ID NO: 2 such that cancer is treated, wherein a Toll-like receptor 3 is naturally expressed in said cell.

5. The method according to claim 4, wherein the cancer is hepatoma, kidney cancer, juvenile pharynx, papilloma, malignant lymphoma, cerebral tumor, glioblastoma, medulloblastoma, astrocytoma, or dermal malignant melanoma.

6. The method according to claim 4, wherein the DNA molecule has the nucleotide sequence from position 1242 to position 1658 of SEQ ID NO: 1.

7. A method for inducing interferon β production in an isolated mammalian cell, the method comprising:
   (i) transfecting an isolated mammalian cell with a vector containing a DNA molecule encoding Toll-like receptor 3; and
   (ii) transfecting said mammalian cell of (i) with a vector containing a DNA molecule encoding a protein that binds to the Toll-like receptor 3, wherein the protein is comprised of the amino acid sequence of SEQ ID NO: 2 or from position 394 to position 352 of SEQ ID NO: 2 and wherein binding of the protein to the Toll-like receptor 3 induces interferon β production in said mammalian cell.

* * * * *